(12) United States Patent
Turner et al.

(10) Patent No.: US 8,361,740 B2
(45) Date of Patent: Jan. 29, 2013

(54) PEPTIDE STANDARDS

(75) Inventors: Charles Turner, London (GB); Raymond Neil Dalton, London (GB)

(73) Assignees: King's College London, London (GB); Guy's and St. Thomas' NHS Foundation Trust, London (GB)

( * ) Notice: Subject to any disclaimer, the term of this patent is extended or adjusted under 35 U.S.C. 154(b) by 442 days.

(21) Appl. No.: 12/597,872

(22) PCT Filed: May 2, 2008

(86) PCT No.: PCT/GB2008/001557
§ 371 (c)(1),
(2), (4) Date: Oct. 27, 2009

(87) PCT Pub. No.: WO2008/135756
PCT Pub. Date: Nov. 13, 2008

(65) Prior Publication Data
US 2010/0159473 A1 Jun. 24, 2010

(30) Foreign Application Priority Data
May 2, 2007 (GB) .................................. 0708529.3

(51) Int. Cl.
C12Q 1/37 (2006.01)
A61K 38/04 (2006.01)
C07K 5/00 (2006.01)
C07K 7/00 (2006.01)
C07K 16/00 (2006.01)
C07K 17/00 (2006.01)

(52) U.S. Cl. ............ 435/24; 530/327; 530/328; 530/329

(58) Field of Classification Search .................. None
See application file for complete search history.

(56) References Cited

FOREIGN PATENT DOCUMENTS
WO 2006/005622 1/2006
WO 2006/099623 9/2006

OTHER PUBLICATIONS

Olsen et al. Trypsin Cleaves Exclusively C-terminal to Arginine and Lysine Residues. Molecular and Cellular Proteomics 3.6, 2004, pp. 608-614.*
Mejia. Letters. Understanding Isotopic Distributions in Mass Spectrometry. JCE. 2006. vol. 83, No. 12, p. 1761.*
Sein. Using Punnett Squares to Facilitate Students' Understanding of Isotopic Distributions in Mass Spectrometry. JCE. 2006, vol. 83, No. 2, pp. 228-232.*
Table of Isotopic Masses and Natural Abundances. 1993-1999. accessed online at http://www.chem.ualberta.ca/~massspec/atomic_mass_abund.pdf on Jun. 1, 2012. 5 pages.*
Pathak et al. Cutting Edge: Editing of Recycling Class II: Peptide Complexes by HLA-DM. J Immunol. 2001. vol. 167, pp. 632-635.*
Anderson et al., Mol. Cell Proteomics, 5:573-588 (2006).
Yu et al., J. Proteome Res., 3:469-477 (2004).
Zhang et al., J. Proteome Res., 1:139-147 (2002).

* cited by examiner

*Primary Examiner* — Marcela M Cordero Garcia
(74) *Attorney, Agent, or Firm* — McAndrews, Held & Malloy, Ltd.

(57) ABSTRACT

The invention relates to methods for making a peptide standard for mass spectrometry said method comprising (a) identifying endopeptidase cleavage sites in a parent polypeptide sequence of interest; (b) selecting peptide sequences from said parent polypeptide which are defined by endopeptidase cleavage sites of step (a); (c) adding a C-terminal extension to each selected sequence; wherein if the endopeptidase cleavage site is C-terminal to its recognition sequence then the C-terminal extension comprises 1 to 6 amino acids, wherein if the endopeptidase cleavage site is N-terminal to its recognition sequence then the C-terminal extension comprises said recognition sequence, wherein if the endopeptidase cleavage site is within its recognition sequence then the C-terminal extension comprises the remainder of said recognition sequence C-terminal to the cleavage site; and (d) synthesizing a peptide having the extended amino acid sequence of step (c). The invention also relates to peptide standards and methods of analysing samples.

13 Claims, 12 Drawing Sheets

PEPTIDE STANDARDS

The present application is filed pursuant to 35 U.S.C. 371 as a U.S. National Phase application of International Patent Application No. PCT/GB08/01557, which was filed May 2, 2008, claiming the benefit of priority to British Patent Application No. 0708529.3, which was filed on May 2, 2007. The entire text of the aforementioned applications is incorporated herein by reference in its entirety.

FIELD OF THE INVENTION

The invention relates to, mass spectrometry (MS), in particular to peptide standards for use in mass spectrometry applications such as tandem MS (MSMS).

BACKGROUND TO THE INVENTION

Typically, MSMS is not used in the art to routinely quantitate proteins. The most common method used for protein detection/quantitation is still immunoassay/ELISA, particularly in clinical settings. Triple quadrupole MSMS is most usually employed for the analysis of small molecules. This is because the molecular weight for effective analysis is limited to approximately 3,000 Daltons. For this reason, the technique is often deemed unsuitable for analysis of proteins which may have much larger masses. Although some other MS techniques may be suitable for proteins, such as MALDI-TOF, MSMS is required for specificity. In order to overcome the difficulties in analysing proteins whose molecular weight exceeds 3,000, these are split into peptides. Relatively short peptides, for example peptides of 8 amino acids, can provide a virtually specific identification of a protein.

In a further development, it is desired to use MSMS for quantitative measurements of protein. The prior art MSMS systems feature only qualitative analysis. At best, prior art attempts have only achieved a semi-quantitative result. In order to achieve quantitation, ideally the whole protein needs to be labelled. This has been attempted in connection with, Apolipoprotein E4. This protein, was produced in an expression system. This is a very expensive and labour intensive technique. The cost of this technique is such that it is prohibitive for routine use.

In MS (such as electrospray MSMS) there are problems related to interference, especially through ion suppression effects. Ion suppression results from the presence of less volatile compounds that can change the efficiency of droplet formation or droplet evaporation, which in turn affects the amount of charged ion in the gas phase that ultimately reaches the detector.

Thus, an important factor that can affect the quantitative performance of a mass detection is ion suppression. Sample matrix, coeluting compounds, and other factors can contribute to this effect. Ionization effects can theoretically occur in either the solution phase or the gas phase. The mass and charge of individual analytes are factors in making a compound a candidate for ion suppression or in making one compound a source of ion suppression for another. It has been shown that molecules with higher mass will suppress the signal of smaller molecules and that more polar analytes are more susceptible to suppression.

The presence of ion suppression or other deleterious effects can be evaluated via experimental protocols. The first involves comparison of (a) the instrument response for calibrators (including any internal standards) injected directly in mobile phase, (b) the same amount of compound added to preextracted samples, and (c) the same amount of compound added to specimen matrix before extraction. The second protocol, which can be viewed as part of interference checks for an assay, involves injection of drugs or metabolites that may also be present in the specimen. Just because a coeluting drug does not produce similar mass fragments does not mean that this compound is incapable of ion suppression.

Another problem with MSMS in the analysis of proteins is a problem of digestion. Typically, the peptides are generated from the protein by endopeptidase action. The industry standard endopeptidase for use in this application is trypsin. Clearly, an efficient or complete trypsin digestion is required in order to successfully reduce the protein to its component peptides for MSMS analysis. For quantitative analysis, it is important that an indication of the digestion is obtained in order to validate the readout of the individual peptide fragments from the target protein. In order to address this problem Anderson and Hunter (2006 Mol Cell Proteomics vol 5 pp 573-88) cloned DNA sequences for clinically important peptides, linked them, and expressed them in a cell free protein expression system with stable isotope arginine and lysine added. This results in a labelled fusion protein consisting of a series of concatenated peptides which should be theoretically separated by the action of trypsin. A problem with this approach is that the concatenated peptides are not equivalent in secondary or tertiary structure to any of the parent polypeptides. A further problem with this approach is that cleavage of the protein is very likely to be sterically hindered by the large number of peptides which have been fused together. Furthermore, the trypsin cleavage site for many of these peptides will be masked in the three dimensional structure of a large fusion protein. Even if these sites can eventually be cleaved, it is likely to be at a low efficiency and perhaps with reaction kinetics which might interfere with the analysis. In addition, Anderson et al report that in use only a minor proportion of the predicted tryptic digest products can be detected (17/30 such peptides were not reproducibly detected according to Anderson). Furthermore, this multi-fused peptide labelling is difficult to perform according to Anderson. Even if this could be reliably reproduced, it still involves a cell free system for the production of the fusion protein. Such systems can suffer from metabolism of lysine or arginine or other amino acids. This makes it more difficult to control the range of products which are produced. Moreover, there is a significant error rate causing introduction of incorrect amino acids into the fused polypeptide product. This is caused at the translation stage so that the mRNA which is introduced may not be accurately translated into protein in such a cell free system, leading to errors in the polypeptide which can be variable and can be as high as several percent of polypeptide product.

Even where this approach has been optimised, the tryptic peptide fragments are typically prepared in parallel, separate from the digestion of the sample to be analysed, and are then 'spiked' into the sample before analysis. Clearly, such an approach is incapable of controlling for endopeptidase action in the sample to be analysed.

The present invention seeks to overcome problems associated with the prior art.

SUMMARY OF THE INVENTION

The present inventors have discovered that the performance of MS can be maximised by provision of internal peptide standards. These peptide standards advantageously correspond closely to tryptic digest product peptides derived from the protein of interest.

In contrast to prior art techniques, the present inventors have surprisingly shown that trypsin has an extremely minimal requirement for C-terminal overhangs in order to produce effective cleavage. Thus, according to the present invention, peptide standards are provided which correspond to the expected tryptic peptide fragments of a protein to be analysed, with the addition of an extremely short C-terminal overhang to allow efficient tryptic digestion. By use of these standards, ion suppression problems can be internally controlled since the peptide species being analysed are identical in amino acid sequences to the peptide standards. Furthermore, these peptide standards provide an internal control for tryptic digestion since it is possible to analyse those peptide standards which have been cleaved by tryptic digest, since they will be missing the extremely short C-terminal amino acid overhang which is provided to "read out" or control for the action of trypsin.

Thus, according to the present invention, low cost peptide standards are provided which are capable of internally controlling ion suppression problems and also internally controlling tryptic digestion problems thereby reliably and cost effectively increasing the efficiency of MS analysis of proteins and peptides.

Thus, in one aspect the invention relates to a method for making a peptide standard for mass spectrometry said method comprising
(a) identifying endopeptidase cleavage sites in a parent polypeptide sequence of interest;
(b) selecting peptide sequences from said parent polypeptide which are defined by the endopeptidase cleavage sites of step (a),
(c) adding a C-terminal extension to each selected sequence, wherein if the endopeptidase cleavage site is C-terminal to its recognition sequence then the C-terminal extension comprises 1 to 6 amino acids,
wherein if the endopeptidase cleavage site is N-terminal to its recognition sequence then the C-terminal extension comprises said recognition sequence,
wherein if the endopeptidase cleavage site is within its recognition sequence then the C-terminal extension comprises the remainder of said recognition sequence C-terminal to the cleavage site; and
(d) synthesising a peptide having the extended amino acid sequence of step (c).

Of course it should be noted that the steps of (c) may be separately (e.g. singly) applied depending on the context. For example, when using an endopeptidase having a cleavage site N-terminal to its recognition sequence then the invention relates to a method as described above wherein said C-terminal extension comprises said recognition sequence. The same applies to the other branches of step (c).

In another embodiment the invention relates to a method for making a peptide standard for mass spectrometry said method comprising
(a) identifying endopeptidase recognition sites in a parent polypeptide sequence of interest;
(b) selecting peptide sequences from said parent polypeptide sequence of interest defined by the endopeptidase recognition sites of step (a), each peptide sequence being selected to include one such endopeptidase recognition site at the C-terminus of each selected peptide sequence;
(c) adding 1 to 6 amino acids to the C-terminus of each selected sequence; and
(d) synthesising a peptide having the amino acid sequence of step (c). This method is advantageously slightly simplified for endopeptidases which cleave C-terminally to their recognition site e.g. trypsin. Preferably said endopeptidase recognition site forms the extreme C-terminal sequence selected in step (b).

The length of the C-terminal extension may be chosen by the operator and may be up to 6 or 7 amino acids or even more. Suitably up to 6 amino acids are used, more suitably up to 5 amino acids are used. Shorter extensions have the advantage of leading to cheaper peptide manufacture. A one amino acid extension is therefore preferred, so long as this is sufficient to allow for efficient cleavage by endopeptidase.

Preferably the continuation sequence of the parent protein is used as the sequence of the C-terminus extension of step (c). Any amino acid sequence may be used as the C-terminal extension. We show that NDCTTM (SEQ ID NO:1) may be used, which demonstrates that any continuation sequence is likely to be suitable. However, most suitably the C-terminal, extension sequence matches the natural continuation amino acid sequence of the parent polypeptide. Preferably cysteine is not present in the C-terminal extension.

Preferably the 1 to 6 amino acids of step (c) are identical to the 1 to 6, amino acids which immediately follow the endopeptidase recognition site in the polypeptide sequence of interest.

Preferably the 1 to 6 amino acids of step (c) are TCVAD (SEQ ID NO:2).

Preferably synthesis of the peptide is by chemical means i.e. chemical peptide synthesis. Preferably synthesis is not by recombinant means which can suffer from extra labour and/or error regarding the nucleic acids used. Preferably synthesis is not by use of a cell free expression system which can suffer from high error rates and/or from problems of metabolism of certain amino acid residues. Preferably chemical synthesis is by the Merrifield synthesis. Clearly the skilled operator may vary the precise synthesis scheme to optimise yields or efficiency or other factors. These features have the advantages of eliminating sources of error such as sequence error in preparation of a nucleotide encoding the amino acid sequence of interest, or transcriptional error in manufacture of mRNA, or metabolism of various amino acid residues, or elimination of labour intensive steps, or a combination of these advantages as explained in more detail below.

Preferably said peptide is labelled with at least one stable isotope, preferably at least two stable isotope(s). Preferably said isotope(s) is/are selected from the group consisting of deuterium, carbon 13, nitrogen 15, and oxygen 18. Preferably said isotope is carbon 13. When two isotopes are used, preferably they are carbon 13 and nitrogen 15. Preferably the stable isotope is incorporated N-terminally with respect to the endopeptidase cleavage site so that the label is retained by the peptide following endopeptidase cleavage.

The endopeptidase is preferably any catalytic entity such as an enzyme or fragment thereof that can break a peptide bond. Currently six groups of protease are defined: serine, threonine, cysteine, aspartic acid, metallo, and glutamic acid. Preferably said endopeptidase is a single endopeptidase. Preferably said endopeptidase is selected from the group consisting of trypsin and V8 endopeptidases, preferably trypsin. Preferably said endopeptidase has a recognition sequence of XXK or XXR.

Preferably the parent polypeptide (polypeptide of interest) is albumin.

Of course, one peptide standard could be used universally to control for endopeptidase digestion in the sample. However, to control for ion suppression the peptide standard used needs to give rise to ions of the same overall structure as those to be detected.

Thus, preferably peptide standards derived from/based on the polypeptide of interest (parent polypeptide) are preferred for use in analysing or detecting said polypeptide.

In another aspect, the invention provides a polypeptide obtainable by a method as described above.

In another aspect, the invention provides a polypeptide which comprises
(i) no more than 25 amino acids
(ii) a stable isotope label
(iii) an endopeptidase recognition site
wherein if the endopeptidase cleavage site is C-terminal to said endopeptidase recognition site then said polypeptide further comprises 1 to 6 amino acid residues between the C-terminal residue of said endopeptidase recognition site and the C-terminus of said polypeptide. Preferably the elements are arranged so that cleavage of the polypeptide by the endopeptidase results in release of at least one amino acid residue from the C-terminal end of the polypeptide, and wherein said stable isotope label is situated N-terminally of the cleavage site.

Preferably said stable isotope is selected from the group consisting of deuterium, carbon 13, nitrogen 15, and oxygen 18. Preferably said isotope is carbon 13.

Preferably said endopeptidase recognition site is a single endopeptidase recognition site. Preferably said endopeptidase is selected from the group consisting of trypsin and V8. Preferably said endopeptidase recognition site is a trypsin recognition site.

Preferably the polypeptide sequence is selected from a parent polypeptide sequence and preferably the 1 to 6 amino acids are selected from the same parent polypeptide sequence. Preferably the 1 to 6 amino acids correspond to the 1 to 6 amino acids which immediately follow the endopeptidase recognition site in said parent polypeptide sequence. Preferably the 1 to 6 amino acids are 1 to 5 amino acids and preferably said 1 to 5 amino acids are TCVAD SEQ ID NO:2). Preferably the parent polypeptide is albumin.

In another aspect, the invention provides a peptide, or a kit comprising one or more peptides, selected from the group consisting, of LVNEVTEFAKTCV (SEQ ID NO:3), LVNEVTEFAKTCVA (SEQ ID NO:4), LVNEVTEFAKTCVAD (SEQ ID NO:5), LVNEVTEFAKNDCTTM (SEQ ID NO:6), and LVNEVTEFAKT (SEQ ID NO:7). Preferably, the last occurring K residue in said peptide is labelled with stable isotope.

In another aspect, the invention provides a peptide, or a kit comprising one or more peptides, selected from the group consisting, of LVNEVTEFAKTCV, LVNEVTEFAKTCVA, LVNEVTEFAKTCVAD, LVNEVTEFAKNDCTTM, and LVNEVTEFAKT. Preferably the last occurring K residue in said peptide is labelled with stable isotope.

In another aspect, the invention provides a method for analysing a sample by mass spectrometry said method comprising providing a sample and a peptide standard as described above, digesting said sample and peptide standard with the appropriate endopeptidase, and subjecting the treated sample and peptide standard to mass spectrometry analysis.

Preferably digesting said sample and peptide standard with the appropriate endopeptidase comprises the steps of
(i) adding said peptide standard to said sample
(ii) contacting the mixture of step (i) with the appropriate endopeptidase.

The appropriate endopeptidase is an endopeptidase which acts via the endopeptidase recognition site. Typically this is the endopeptidase whose recognition site is comprised by the peptide standard of the invention i.e the cognate endopeptidase. However, it is possible that a different endopeptidase may be used which recognises the same site, or which recognises a site which is also present such as a smaller site within the endopeptidase site incorporated into the peptide standard of the invention. Preferably the appropriate endopeptidase is the endopeptidase whose recognition site is comprised by the peptide standard of the invention.

DETAILED DESCRIPTION OF THE INVENTION

Quantitative metabolite assays using MSMS rely on stable isotope dilution techniques, where a constant amount of a stable isotope of the compound of interest is added at an early stage of the analysis to correct for any processing losses/changes, ionisation efficiency, fragmentation efficiency, and detection variability. The stable isotope signal acts as a ruler and the concentration of the metabolite in the original sample is a function (usually linear) of the isotope ratio.

The ideal internal standardisation material for any MSMS based quantitative protein measurement is the protein in question appropriately labelled with stable isotope amino acids. In peptide based analysis, in theory every peptide being measured would need to be labelled. In the case of proteolytic digestion using trypsin the cleavage is predictable, at the C-terminal peptide bond of lysine or arginine. Hence, for trypsin, stable isotope labelling of just lysine and arginine ensures that all peptides released are stable isotope labelled at the C-terminus and, because it is an arginine/lysine, the charge is localised to provide, on MSMS, an informative y series sequence where each y fragment contains the label and, therefore, an informative multiple reaction monitoring (MRM) transition. However, the cost of such an approach is prohibitive.

The simplest and cheapest approach to the problem is to use a stable isotope labelled peptide of the peptide to be measured. This allows for any of the processing losses etc (see above) post digestion and, therefore, does not control for the digestion itself; a crucial stage, particularly in routine clinical analysis where incubation times will need to be minimised. Anderson and Hunter (ibid.) have made multiple concatenated peptide constructs, using cloning and expression systems. In theory, these should enable the measurement of multiple proteins simultaneously. Clearly these products demonstrate proteolysis but are costly and not equivalent to the original protein, so there remain problems of efficiency because of the complexity of the constructs, and problems of errors and consistency of the final products.

According to the invention, we propose a simpler and more generally applicable solution to these problems. Considering the structure of endopeptidases such as the enzyme trypsin and the functional process of proteolysis it became clear to us that at any protein cleavage site it is, apart from the lysine/arginine residue fitting in the active site pocket, the amino acids N-terminal to the site that affect binding of the protein and, consequently, one should only need the next C-terminal amino acid to allow correction for the proteolytic process. Aspects of the invention are based on this key finding.

MS Applications

Mass spectrometry (MS) is a powerful qualitative and quantitative analytical technique that has been introduced into many clinical and research laboratories during the last 5 years. The cost of MS analyzers has dropped to a range that is affordable for a majority of laboratories. There is a greater awareness of the laboratory applications of MS in the clinical laboratory, so that technical support and assay development are high priorities. In the clinical laboratory, mass spectrometers are used to measure a wide range of clinically relevant analytes. When applied to biological samples, the power of MS lies in its selectivity toward the identification and quantification of compounds. The combination of gas chromatography or HPLC with MS yields a particularly powerful tool. This is especially so for HPLC-MS or HPLC-tandem MS, which is the reason that this combination is being used by many clinical laboratories.

In particular, the invention involves the use of MSMS as a powerful tool to identify the presence of specific proteins, peptides and protein variants in biological fluids. The interest is because of the increasing use of specific proteins and peptides as indicators of disease states or likely onset of disease states.

There is increasing interest in quantitative measurement of proteins by MSMS. Using tryptic digestion and peptide targeted multiple reaction monitoring (MRM) mode it is easy to detect the presence/absence of a peptide, but accurate quantitation requires a stable isotope labelled internal standard. This is necessary to correct for analytical variables, primarily tryptic digestion and ion suppression.

We disclose a simple, flexible, and cost effective approach that addresses these issues.

To take into account ion suppression the standards are stable isotope labelled.

The present invention relates to standards that take into account the protein digestion and ion suppression problems. The standards are cheap and easy to synthesise.

Peptide Standards and Internal Peptide Standards

Co-digestion of the peptide standard and the sample to be analysed has the advantage of controlling for endopeptidase action internally within the actual sample being analysed. Thus, preferably the peptide standard of the invention and the sample are always co-digested in order to control for digestion efficacy and/or metabolic features of the digestion reaction/incubation step. This co-digestion application is referred to as use as an internal peptide standard for the reasons noted above. Thus the invention relates to use of peptide standards as described above as internal peptide standards.

Clearly, use as an internal peptide standard brings many benefits. However, the peptide standards of the invention may also be used as conventional peptide standards i.e. simply added to ('spiked' into) the sample before analysis. In this embodiment, the peptide standard is not co-digested with the sample but is merely added into the already digested sample and then analysed. In this embodiment the peptide standard itself may not even be cleaved—it will typically be analysed in the state in which it is when spiked into the sample. Thus the invention relates to use of peptide standards as described above as conventional peptide standards.

In conventional peptide standard embodiments, assumptions may need to be made about the digestion since there is no 'internal' control for digestion in such applications. Therefore inferences drawn from the results depend on knowledge of exactly how much peptide standard was added to the sample.

In internal peptide standard embodiments calculations may be made based on the isotope ratio, for example by producing a calibration curve and using the isotope ratio in calculation of concentrations. This is an advantage of the preferred internal peptide standard embodiments of the invention.

Advantages

The invention advantageously addresses the twin problems of controlling for protein digestion and ion suppression.

It is an advantage of the peptide standards of the present invention that the cleavage site is presented to the endopeptidase. Prior art concatenation techniques suffer from the problem of burying, masking or sterically hindering access to the endopeptidase recognition site. This problem is advantageously overcome using the peptide standards according to the present invention.

Prior art cell free synthesis is an expensive and time consuming process. The individual peptide standards of the present invention are cheaper and easier to manufacture, which is an advantage of the present invention.

It is an advantage of the present invention that the naturally occurring peptide sequences may be retained. In particular, in some embodiments, the naturally occurring sequence of the peptide of interest can even be retained in the C-terminal overhang (C-terminal extension) which follows the endopeptidase cleavage site in the peptide standards of the present invention. This has the advantageous feature of presenting the naturally occurring endopeptidase recognition site in the context of its naturally occurring neighbouring amino acids, thereby providing another level of internal control for the endopeptidase action in the sample being analysed.

A further advantage of the present invention flows from the chemical synthesis of the peptides of interest. This advantageously avoids a nucleic acid step in the polypeptide production. A nucleic acid step inevitably requires extra labour and cost. Furthermore, it introduces further opportunities for errors to be introduced into the system, for example errors in the nucleotide sequence of the nucleic acid being used to encode the peptide standard. Thus, embodiments of the invention which avoid transcriptional or translational production of the peptide standards bring further advantages. Thus, chemical synthesis of the peptide standards of the invention is preferred.

In one embodiment, preferably the peptide standards of the present invention are not derived from plasma proteins. Thus, preferably the peptide standards of the present invention are for non plasma proteins.

Manufacture of polypeptides in biological cell free systems brings problems of metabolism of certain amino acids. Thus, it is very difficult to control the products which are produced. In addition to this, there is a significant naturally occurring error rate associated with expression and cell free systems which can lead to a percentage of the products having incorrect amino acids incorporated. The peptide standards of the present invention advantageously alleviate one or more of these problems.

Prior art techniques frequently involve a chromatography step. Advantageously, using the peptide standards of the present invention enables the elimination, for some important clinical applications, of this laborious step.

It is an advantage of the invention that chromatography steps can be eliminated.

It is an advantage of the invention that it helps to eliminate problems caused by matrix changes (e.g. sick patients).

Making a Peptide

The methods of the invention require the making of the peptide standards. The first step in this process is to decide upon the sequence of the peptide standard itself. As a first step, endopeptidase recognition sites are identified in a parent polypeptide sequence of interest. The parent polypeptide sequence of interest is simply the entity which it is desired to study in the sample. This could be any polypeptide which it is desired to analyse. Regarding the endopeptidase, this can be any endopeptidase suitable for use in digestion of polypeptides. Exemplary endopeptidases are discussed in more detail below. In order to identify endopeptidase recognition sites in the parent polypeptide sequence, a sequence comparison is made between the endopeptidase recognition site and the parent polypeptide sequence. This may be done manually, by reading the polypeptide sequence and marking at each trypsin cleavage site, or may be conveniently automated using any of a wide range of sequence analysis tools which are both freely and commercially available such as "CLC Protein Workbench" or the Genetics Computer Group (GCG) Wisconsin package. With reference to FIG. 1, part A represents a diagram of the parent polypeptide with the N-terminus at the left and C-terminus at the right. After the identification step, the parent polypeptide sequence is as shown in part B. Each of the small vertical lines marked on the sequence represents an endopeptidase recognition site.

The next step is the selecting of peptide sequences from the parent polypeptide, which peptide sequences are defined by the endopeptidase recognition or cleavage sites. In overview, a peptide sequence defined by the endopeptidase recognition sites is simply a peptide having or consisting of the parent polypeptide amino acid sequence in between two endopeptidase recognition sites, preferably between two endopeptidase cleavage sites, preferably two neighbouring endopeptidase recognition/cleavage sites. With reference to FIG. 1, part C shows the selected sequences defined by the endopeptidase cleavage sites. Preferably the sequence so selected does not include the recognition site at its N-terminus. Preferably the sequence so selected begins at the cut site, i.e. the first amino acid C-terminal of the cut site is the first amino acid of each peptide sequence so selected. For example, when the endopeptidase is trypsin, the peptide selected will not include an arginine residue or a lysine residue at its N-terminus, but will begin with the first amino acid after said Arg/Lys residue. Preferably the peptide so selected runs up to the endopeptidase cut site at its C-terminus i.e. the last amino acid N-terminal of that cut site is the last amino acid so selected. Thus, when the endopeptidase is trypsin, the C-terminus of the peptide so selected will terminate in the last amino acid of said endopeptidase recognition site since the trypsin cut site is immediately after its recognition site. For example, when the endopeptidase is trypsin, the sequence so selected will terminate in a lysine or an arginine residue.

The next step is to add a C-terminal extension to each selected sequence.

When the cleavage site and recognition site coterminate i.e. when cleavage takes place immediately after (i.e. C-terminal to) the last amino acid of the recognition site (e.g. ABCD/ where '/' indicates the cut or cleavage site), then preferably adding a C-terminal extension comprises adding one to five amino acids to the C-terminus of each selected sequence. These amino acids can be any amino acids chosen by the operator. Preferably these amino acids do not comprise lysine or arginine. Preferably these amino acids correspond to the equivalent amino acids from the parent polypeptide.

When cleavage occurs within the endopeptidase recognition site or before (i.e. N-terminal to) the first amino acid of the recognition site (e.g. ABC/D, AB/CD, A/BCD or /ABCD where '/' indicates the cut or cleavage site), preferably adding a C-terminal extension comprises adding the amino acid(s) making up the (or the remainder of the) recognition site to the C-terminus of said site for each selected sequence. Optionally further amino acid(s) may be added if so desired.

The C-terminal extension is discussed in more detail below.

With reference to FIG. 1, part D shows the resulting peptide sequences with C-terminal extensions. In part D, the C-terminal extension is represented by X(n) where X means any amino acid and n is an integer from 1 to 6.

In order to make the peptide standard according to the invention, the selected peptide sequence together with its C-terminal extension is then synthesised as a single contiguous peptide. Preferably this is accomplished by any suitable chemical synthesis method known in the art such as those used in the examples section.

N-Terminus of Parent Polypeptide

As will be apparent from the above discussion, the N-terminus of the parent polypeptide will be defined at one end by the N-terminus itself (i.e. the NH2 group on the first amino acid of the parent polypeptide) and at the other end will be defined by the first endopeptidase recognition site encountered in the parent polypeptide. For the purposes of the present invention, this N-terminal peptide can be treated exactly as an internal peptide which is defined by an endopeptidase site at each end as described above. The C-terminal extension is simply added to the C-terminus of this peptide as with any other peptide defined by two internal endopeptidase sites.

C-Terminus of Parent Polypeptide

As will be apparent from the above discussion, the C-terminus of the parent polypeptide has to be treated slightly differently from the internal polypeptides of the N-terminal polypeptides which may all be treated in the same fashion as outlined above. Considering the C-terminal peptide, this is defined at its N-terminal end by the last occurring internal endopeptidase site, and is defined at its C-terminal end by the COOH group of the last amino acid of the parent polypeptide. Clearly, it is improbable that the C-terminal amino acids of the parent polypeptide would in fact form an endopeptidase recognition site, although it is theoretically possible that they would. However, for the majority of proteins, the C-terminal amino acids will not form an endopeptidase recognition site. Therefore, adding a C-terminal extension beyond the C-terminus of the protein would not lead to a cleavable peptide standard useful for mass spectrometry, the reason being that such a peptide would not be cleaved by an endopeptidase since it would not comprise an endopeptidase recognition site. Therefore, preferably a peptide standard according to the present invention is not formed from the extreme C-terminus of the parent polypeptide. Thus, preferably a peptide sequence defined by the endopeptidase recognition/cleavage sites as described herein refers to, a peptide sequence which is flanked at each end by an endopeptidase recognition/cleavage site, or is flanked at one end by the N-terminus of the parent polypeptide and at the other end by an internal endopeptidase site.

It is possible to make a peptide standard according to the present invention from the extreme C-terminus of the parent polypeptide. This situation is shown in FIG. 1 part E. In this situation, the extreme C-terminal peptide defined at one end by the extreme C-terminus of the parent polypeptide and at the other by the last occurring endopeptidase recognition site is taken together with the second last peptide defined by the endopeptidase recognition sites. This combined sequence can then be synthesised and used as an internal peptide standard since cleavage by the endopeptidase of interest will result in the C-terminus peptide and its immediate neighbouring peptide being generated by the action of the endopeptidase. In this embodiment, it is advantageous to ensure that a stable isotopic label is included into at least two amino acid residues, at least one of which must be N-terminal of the endopeptidase recognition site, and at least one must be C-terminal of that site, so that following endopeptidase cleavage each of the resulting peptide standards is labelled and can be identified in the MS output.

Preferably, peptide standards according to the invention are not produced from the extreme C-terminus end of the parent polypeptide. Preferably, peptide standards according to the present invention are produced from peptides defined at each end by reference to an internal endopeptidase recognition/cleavage site, or from peptides defined at one end by the extreme N-terminus of the parent polypeptide and at the other end by reference to an endopeptidase recognition/cleavage site.

C-Terminal Extension

The C-terminal extension is a key feature of the peptide standards of the present invention. This feature is central to the internal control of endopeptidase action. The term 'C-terminal extension' reflects the way in which the peptide standard sequence is designed as discussed herein—in essence the 'C-terminal extension' refers to those amino acids of the peptide standard which follow the last residue before the C-terminal cleavage site. It should be noted that the C-terminal extension may itself comprise amino acids derived from the parent sequence. For the internal control of endopeptidase action in samples for MS analysis, it is an essential feature that the peptide standards of the invention have a C-terminal extension of at least one amino acid following the cleavage site of the endopeptidase so that cleaved and uncleaved ions may be distinguished. In use, upon incubation with the cognate endopeptidase this C-terminal extension is cleaved from the remainder of the peptide standard. The loss of this C-terminal extension is detected by the mass spectroscopy and therefore the action of the endopeptidase is internally controlled. This is an important and advantageous feature of the present invention.

The length and/or composition of the C-terminal extension is chosen to firstly allow discrimination between the cleaved and uncleaved ions in MS analysis, and secondly to permit efficient cleavage by the cognate endopeptidase. In practice, a C-terminal extension of any single amino acid is sufficient to allow discrimination between the cleaved and uncleaved ions since the loss of a known amino acid residue from the detected ion provides a clear and easily distinguished mass difference between the intact and cleaved forms. Hence the C-terminal extension is preferably at least one amino acid in length. In order to produce efficient cleavage by the endopeptidase, the length and/or composition of the C-terminal extension may need to be carefully chosen paying attention to the requirements of the endopeptidase of choice. In the case of trypsin, the present inventors have surprisingly found that this endopeptidase can tolerate an extremely short C-terminal extension such as only a single amino acid. However, it may be that other endopeptidases may require a longer C-terminal extension, or a specific composition. For example, some endopeptidases may require the presence of amino acids beyond their cut site and in these circumstances the peptide standard C-terminal extension preferably comprises same.

In some embodiments it may be possible that a particular endopeptidase has a recognition site which extends C-terminally of the cleavage site. For example, the recognition site may be ABCD/EFG where '/' represents the cleavage site. (This is in contrast to the situation in which the cleavage site and the recognition site co-terminate such as for trypsin e.g. ABCD/). In this situation (i.e. recognition site which extends C-terminally of the cleavage site), clearly the recognition site has to be present on the peptide standard in order to obtain efficient cleavage. Therefore, in this embodiment the C-terminal extension may be chosen to be that part of the recognition site beyond the cut site for inclusion in the peptide standard. In other words, the C-terminal extension in embodiments where the recognition site of the endopeptidase extends C-terminally of the cleavage site is preferably chosen to be those amino acids present in the recognition site C-terminal of the cleavage site. In this embodiment it may be that the peptide standard would not need to include any amino acids beyond the recognition site since the distal (C-terminal) part of that recognition site forms the 'C-terminal extension' i.e. that part which is lost following endopeptidase action thereby allowing differentiation of the cleaved and uncleaved peptide ions.

In other words, when the endopeptidase is trypsin, the C-terminal extension amino acids should preferably be the C to N sequence of the next tryptic peptide, hence for albumin the TCAVD (SEQ ID NO:2) sequence from T7. In some embodiments the C-terminal extension may comprise sequence unrelated to the parent peptide, such as the NDCTTM hexapeptide (SEQ ID NO:1)—we demonstrate that, in terms of testing for trypsin action, the C-terminal extension sequence is extremely flexible. The C-terminal extension, such as a single amino acid extension, can be any that does not interfere with standard endopeptidase (such as trypsin) digestion.

Thus, the C-terminal extension will typically be determined by the operator with reference to the guidance given above. It must be at least one amino acid long. It must be sufficiently long to support endopeptidase action, which is easily determined by routine trial and error if necessary. It must be of a composition which promotes, or at least does not prevent, endopeptidase action which again can be easily determined by routine trial and error if necessary. Preferably the sequence of the C-terminal extension follows the sequence of the parent polypeptide immediately after the endopeptidase cleavage site.

The C-terminal extension may be any suitable length, particularly with reference to the guidance given herein regarding peptide standard lengths, for example the C-terminal extension may be 1 to 21 amino acids, 1 to 15 amino acids, 1 to 10 amino acids, 1 to 9 amino acids, 1 to 8 amino acids, 1 to 7 amino acids, 1 to 6 amino acids or even fewer. When the endopeptidase cleavage site is C-terminal to the endopeptidase recognition site, preferably the C-terminal extension is 1 to 6 amino acids, more preferably the C-terminal extension is 1 to 5 amino acids; preferably these 1 to 5 amino acids are, or are selected from, TCVAD (SEQ ID NO:2) or NDCT (SEQ ID NO:8), preferably from TCVAD (SEQ ID NO:2). When selecting fewer than 5, amino acids, preferably they are selected in the N to C terminal direction from the given sequences. Preferably the C-terminal extension is 1 to 5 amino acids; preferably the C-terminal extension is 1 to 4 amino acids; preferably the C-terminal extension is 1 to 3 amino acids; preferably the C-terminal extension is 1 or 2 amino acids; preferably the C-terminal extension is 1 amino acid—this has the advantage of minimising peptide length whilst retaining the ability to control for endopeptidase action. Preferably the C-terminal extension does not contain cysteine. If the C-terminal extension does contain cysteine, preferably it is not the terminal amino acid residue. If the C-terminal extension does contain cysteine, preferably there is at least one further amino acid C-terminal of the last occurring cysteine.

Peptide Lengths

Due to the nature of the mass spectrometric analysis, shorter peptides are more desirable. Shorter peptides have the advantage of being cheaper and easier to make, easier to handle and more tractable. In general, shorter is better for at least these reasons. However, the peptide needs to be of sufficient length such that its detection in MS yields meaningful information about the identity of the parent polypeptide. If the peptide is too short, for example, only two or three amino acids, then the probability is that such a short sequence might occur in many possible candidate polypeptides and therefore detection of such a short peptide may not be effective in indicating the presence of the parent polypeptide in the sample. Therefore, the peptide standard of the invention must be sufficiently long to allow it to function as an identifier of the parent polypeptide. In practice, a peptide of approximately 8 amino acids or longer will typically uniquely identify the parent polypeptide from which it was derived. Thus, preferably the peptide standards of the invention are at least 8 amino acids in length.

Preferably the peptide standard is at least 4 amino acids, preferably at least 5 amino acids, preferably at least 6 amino acids, preferably at least 7 amino acids, preferably at least 8 amino acids, preferably at least 9 amino acids, preferably at least 10 amino acids, preferably at least 12 amino acids or even more.

The peptide lengths given herein preferably relate to the length of the entire peptide standard, i.e. they include any C-terminal extension amino acids which may have been added in the designing of the sequence of said peptide standard.

As noted above, the longer peptides are technically more difficult to manufacture and add cost and labour to the process. Therefore, in general, shorter peptides are preferred. Preferably the peptide standard of the invention is 100 amino acids or less, preferably 50 amino acids or less, preferably 30 amino acids or less, preferably 28 amino acids or less, preferably 26 amino acids, or less, preferably 25 amino acids or less, preferably 24 amino acids or less, preferably 23 amino acids or less, preferably 22 amino acids or less, preferably 21 amino acids or less, preferably 20 amino acids or even less.

Thus, the most preferred peptide standards according to the invention combine sufficient length to uniquely identify the parent polypeptide together with a restricted overall length which enables them to be cheaply and efficiently produced. For these reasons, preferably peptide standards according to the invention are from 6 to 26 amino acids in length, preferably from 8 to 24 amino acids in length, preferably from 10 to 22 amino acids in length, preferably from 12 to 20 amino acids in length, preferably from 14 to 18 amino acids in length, preferably approximately 16 amino acids in length. Most preferred lengths (and ranges) are as shown in the examples section.

In a preferred embodiment of the invention, the step of selecting peptide sequences from the parent polypeptide sequence of interest defined by the endopeptidase recognition sites further comprises the step of selecting the shortest endopeptidase fragments of that protein of interest, preferably the shortest fragments of at least five amino acids in length, preferably the shortest fragments of at least 8 amino acids in length. Preferably the peptide sequences defined by the endopeptidase recognition sites are selected from amongst the shortest peptide sequences so defined.

In selecting a peptide standard sequence from a parent polypeptide (such as albumin), other criteria may advantageously be applied.

One such criterion relates to whether the peptide is unique/informative the target polypeptide such as albumin. This may be a factor of the complexity of the sequence or the frequency of occurrence of such, peptide sequences in the sample being analysed, for example peptides corresponding to frequently repeated sequences would be less suitable than 'rare' sequences which are more likely to be unique to the target protein and thus of higher informational value if detected.

Another such criterion relates to the level of initial ionisation; the greater the doubly charged ions the more sensitive the system and/or the better the fragmentation.

Another such criterion relates to the ability to generate a reasonable product ion scan and/or select a high sensitivity transition (MRM).

Usually a peptide of 4-24 amino acids will fulfil the criteria noted above. Determination of whether or not such criteria are met may be made by the skilled operator according to the guidance presented herein.

Endopeptidases

Preferred endopeptidases are those having a defined recognition site. Especially preferred are endopeptidases such as trypsin, or V8 endopeptidase. Most preferred is trypsin. Trypsin has the advantage of being the industry standard for preparation of peptides (sometimes referred to as 'internal' peptide fragments) from larger polypeptides or proteins, for mass spectrometric analysis. Trypsin also has the advantageous feature of cutting frequently within a given polypeptide sequence so that small peptide sequences are likely to be defined by the occurrence of its recognition sites in the parent polypeptide of interest.

Polypeptides of Interest

The polypeptide of interest will be any polypeptide which it is desired to detect by mass spectrometry. Typically polypeptides of interest are those which may be found in body fluids of a patient such as serum, saliva, or urine. Most preferred is albumin. In particular, the invention finds application in the provision of peptide standards for use in aiding the diagnosis of albuminuria.

Sample

Preferably the sample comprises the target polypeptide of interest at 1000 mg/litre or less, preferably at 100 mg/litre or less, preferably at 25 mg/litre or less, preferably at 1 mg/litre or less. Most preferred is target polypeptide of interest at a concentration of approximately 25-1000 mg/litre. When the target polypeptide of interest is albumin, preferably it is present at about 1 mg/litre. Clearly preparation of dilutions to the appropriate level is a matter for the operator.

By way of illustration, the sample may comprise or consist of plasma. When the sample is plasma, and the target polypeptide is albumin, the target polypeptide is present in an initial concentration 40 g/l (40,000 mg/l). Thus, an initial dilution of 1:40 would be appropriate. Clearly, when the target polypeptide is a lower concentration protein, for example retinol binding protein, then the optimal initial dilution may be correspondingly lower e.g. 1:5.

Preferably the peptide standards of the present invention are applied to samples at a final assay concentration of approx. 10 to 20 umol/litre. Preferred values are given in the examples section.

The concentration of the internal standard is preferably equivalent to or higher than the average concentration of the peptide to be measured. Thus, values given in the examples such as 10 to 20 umol/l are typically convenient to accurately measure the concentration of peptide, after tryptic digestion.

Label

The label is preferably a stable isotopic label. This leads to a mass difference between the peptide standard and the unlabelled peptide of identical amino acid composition derived from the target polypeptide in the sample.

Preferably arginine and/or lysine residues are labelled.

Further Applications

The invention finds application in the MS analysis of polypeptides/proteins. This may be qualitative or quantitative. Detection of biomarkers by MS, genotyping (i.e. detection of protein polymorphisms and inferring genotype from same), and any other related MS applications benefit from the use of peptide standards and methods of the present invention.

Tandem MS ('MSMS') for peptide analysis and related MS technologies are well known to the person skilled in the art.

The invention finds application in quantitative measurement of clinically significant biomarkers using electrospray mass spectrometry-mass spectrometry (MSMS).

Analysis using singly charged peptides typically permits analysis in a mass range of 0-2000 daltons (m/z) on a typical machine. More sophisticated machines can provide a range of 0-3000 daltons (m/z). In analysis methods according to the present invention it is preferred to use doubly charged peptide analysis. This provides benefits such as better fragmentation and also advantageously extends the workable mass range of analysis e.g. by doubling it. Thus, by analysing doubly charged peptides, a mass range of 0-4000 daltons (m/z) may be obtained on a typical machine, or 0-6000 daltons (m/z) on more sophisticated machines. Thus the invention may be applied using doubly charged peptides for MRM analysis—this takes, the potential mass range to 6000 daltons.

The invention finds application in current reference to quantitative peptide based measurement of protein biomarkers using protease (e.g. trypsin) digestion.

The peptide standards of the invention need not correspond precisely to the target peptide being detected. For example, peptide standards based on the T6 albumin may be used as peptide standards for analysis of any other peptides such as non-T6 peptides.

It is a benefit of the invention that digestion efficacy can be internally checked (controlled for) in the sample being analysed. Of course in some applications the peptide standard sequences may be digested more rapidly than the whole protein. This is to be expected, on purely thermodynamic grounds. Consequently, the peptide standard will not always control for quantitative digestion efficiency; nevertheless the peptide standard digestion is an important check of digestion efficacy, i.e. that effective digestion has occurred. This control advantageously provides an indication that digestion has occurred, and that consistent digestion has occurred. This control advantageously provides a control for reproducibility.

For quantitative applications; preferably at least three peptides per protein are assayed. This has the advantage of avoiding confounding of the results due to protein polymorphism effects.

Preferably at least two transitions per peptide are assayed, preferably at least three transitions per peptide are assayed.

Preferably peptide standards of the invention are derived from conserved regions of the parent polypeptide of interest.

The present invention may advantageously be applied to the determination of genetic polymorphisms. In this embodiment, preferably peptides derived from the polymorphic region are analysed. The characteristics of a peptide having a certain amino acid polymorphism can be predicted, and the presence or absence of these species can be used to infer whether or not the subject from which the sample was taken is homozygous or heterozygous for a particular allele. Typically, this will be performed quantitatively so that a ratio of 100 to 0 would indicate homozygosity for the first allele, a ratio of 50 to 50 would indicate heterozygosity, and a ratio of 0 to 100 would indicate homozygosity for the second allele. Furthermore, observing a ratio of 0 (i.e. absence) of a particular allele can itself provide useful information by indicating that the subject does not possess that allele, even if other possible allele(s) are not interrogated at that time.

MSMS has been shown to be effective in identifying protein variants that are responsible for several genetic disease conditions such as sickle cell anaemia. The method of identifying protein variants involves knowledge of the gene sequence of the normal and variant, use of enzymatic digestion of the protein and the focusing on specific fragments containing variants.

The invention may be usefully applied to multiplexing applications. In this scenario, multiple peptide standards derived from multiple parent polypeptides may be included into the same sample, or into the same kit. This has the advantage of allowing internal control and standardisation for the detection of multiple target protein species from a single sample.

As an alternative, peptide standards having, the same amino acid sequence may be used in multiplexing applications such as concentration multiplexing (see below). In this embodiment, the peptides differ in respect of the stable isotope label. This may be a difference of degree (e.g. same label, different numbers of atoms per peptide) or a qualitative difference (e.g. different stable isotope labels used in 2 different peptides of the same sequence). So long as the final masses of the cleaved peptides differ to allow differentiation, the particular mode of achieving this variation is a matter for the operator.

A further multiplexing application is in the provision of standards at multiple different concentrations. In this embodiment, different peptide standards according to the invention would be included in the standards or kits of the invention at different concentrations. This has the advantage of allowing samples and turning different concentrations of the target species to be controlled by addition of a single aliquot of the peptide standard or mixture. This is because for effective mass spectrometry the sample has to be diluted to leave a target polypeptide within a particular concentration range to facilitate detection. If at the outset the concentration of the target polypeptide in the sample is not known, then dosing the sample of the appropriate concentration of peptide standard can be difficult. By including, different peptide standards at different concentrations, then the same sample could be diluted over many orders of magnitude and the operator may simply select the peptide standard of the appropriate concentration/dilution in order to control that particular sample retrospectively. This has the advantage of not having to determine the initial concentration of the target polypeptide for detection before dosing the sample with the peptide standard. Thus, this eliminates wasteful 'tester' analysis by allowing multiple target protein concentrations to be controlled by the administration of a single dose of peptide standards.

Thus the invention also relates to kit(s) comprising two or more peptide standards according to the present invention derived from two or more different target/parent peptides. Furthermore, the invention also relates to kit(s) comprising peptide standards at two or more concentrations. In a preferred embodiment the invention relates to one or more aliquot(s) of peptide standards, each aliquot comprising two or more different peptide standards, each peptide standard being at a different concentration within said aliquot, thereby advantageously allowing analysis of a range of different target polypeptide concentrations by single dosing of MS sample from said aliquot.

It will be apparent to a skilled reader that the operation of the invention has been described in the 'C-terminal' mode for ease of understanding. Clearly, this could be reversed/inverted and the invention could be operated in the 'N-terminal' mode. In this scenario, the skilled worker would simply adjust the construction of the peptides/methods accordingly according to the principles set out herein. For example, in N-terminal mode the cleavage would be N-terminal, the peptides would have N-terminal extensions, the N-terminal amino acid(s) would be removed by cleavage thereby controlling for digestion, the stable isotope label would need to be placed C-terminally of the cleavage site to be retained by the cleaved peptide standard and so on. Reversal/inversion in this manner is within the abilities of the skilled person in view of the guidance given herein.

The invention is now described by way of example. These examples are not intended to be limiting, but are rather illustrative in nature. In the examples, reference is made to the following figures.

BRIEF DESCRIPTION OF THE FIGURES

FIG. 1 shows a diagram.

EXAMPLES

Example 1

Peptide Standard Digestion and MS Analysis

Figure 2:
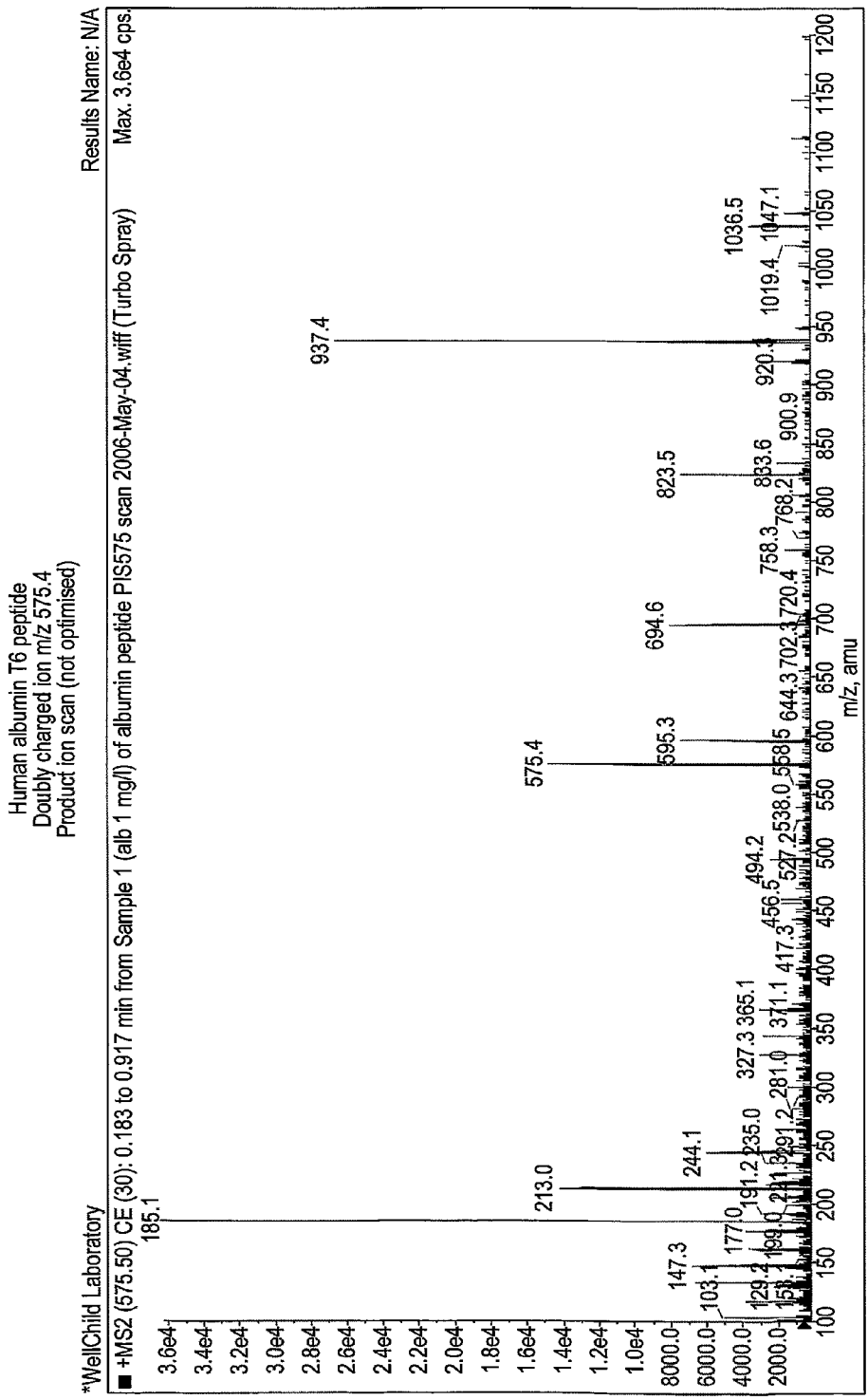
FIGS. 2 to 10 show graphs.
Figure 3:
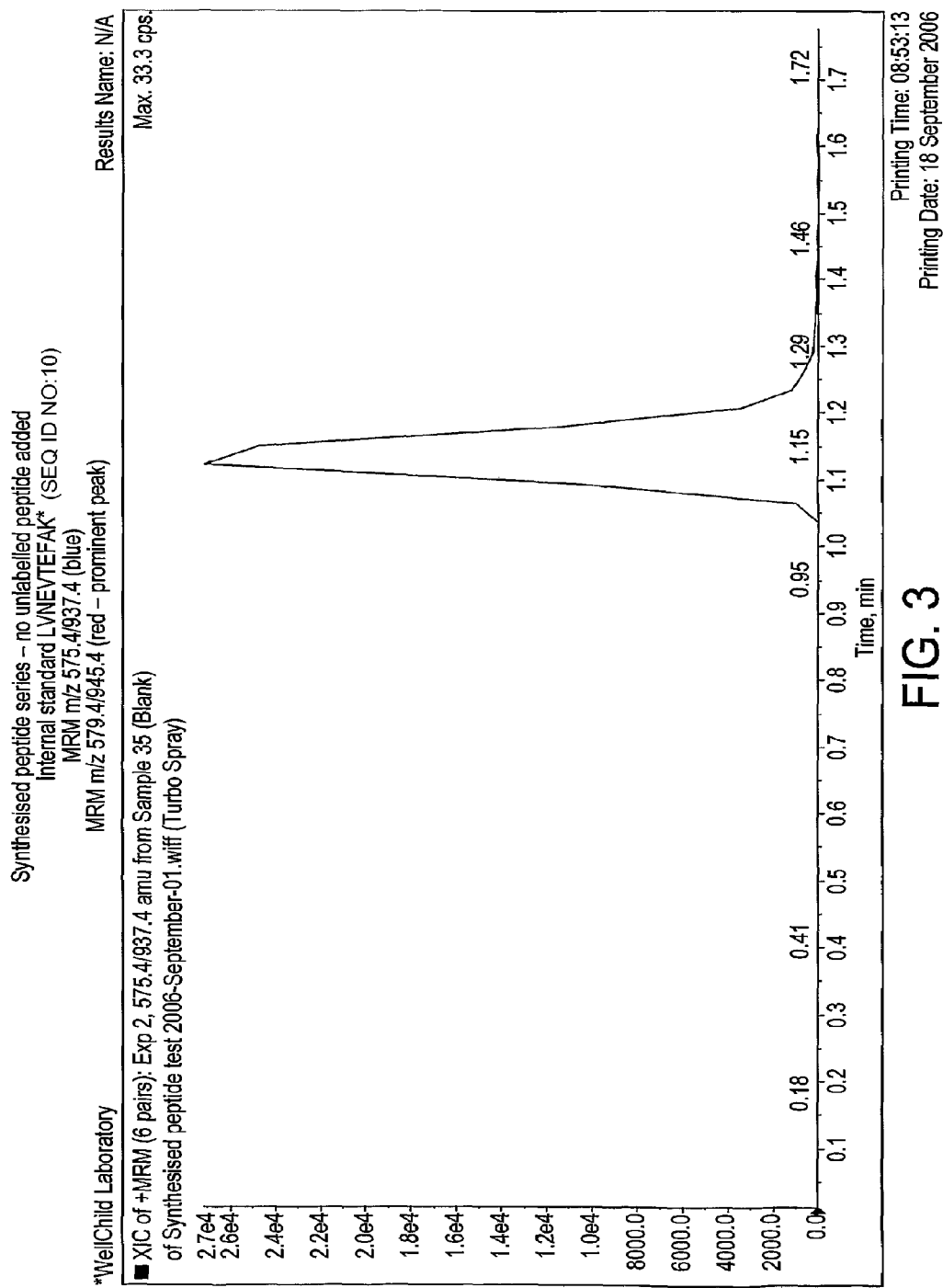
Figure 4:
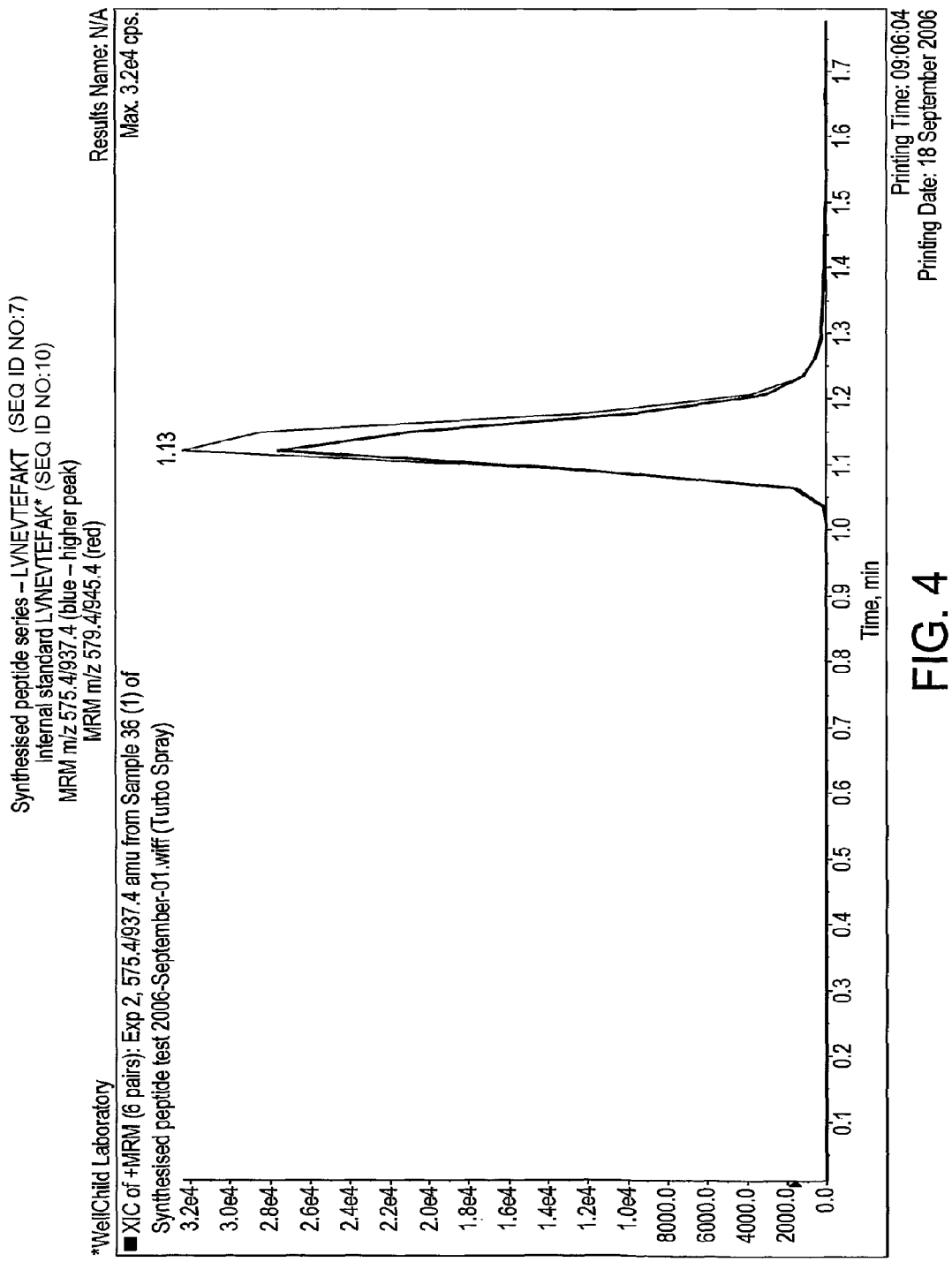
Figure 5:
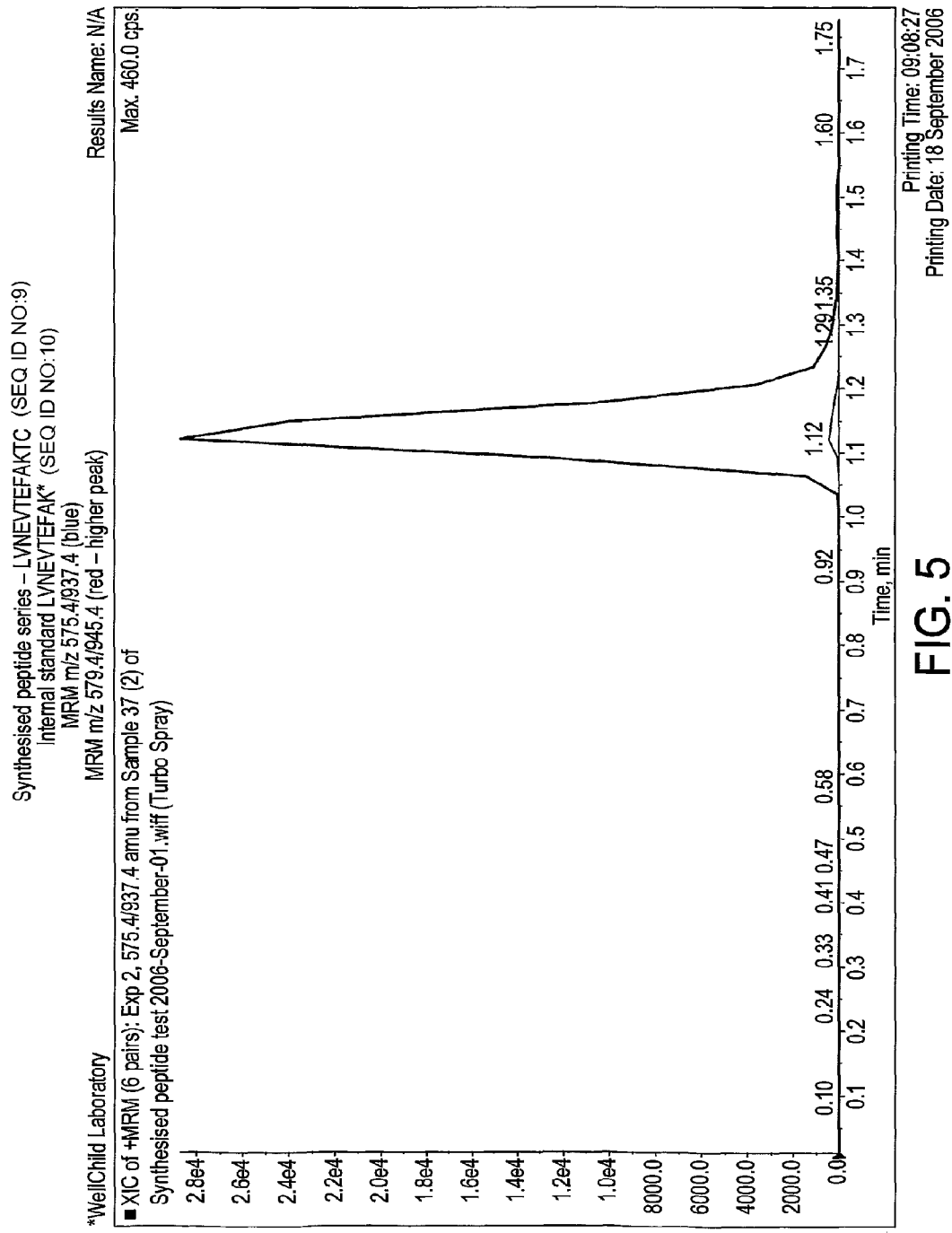
Figure 6:
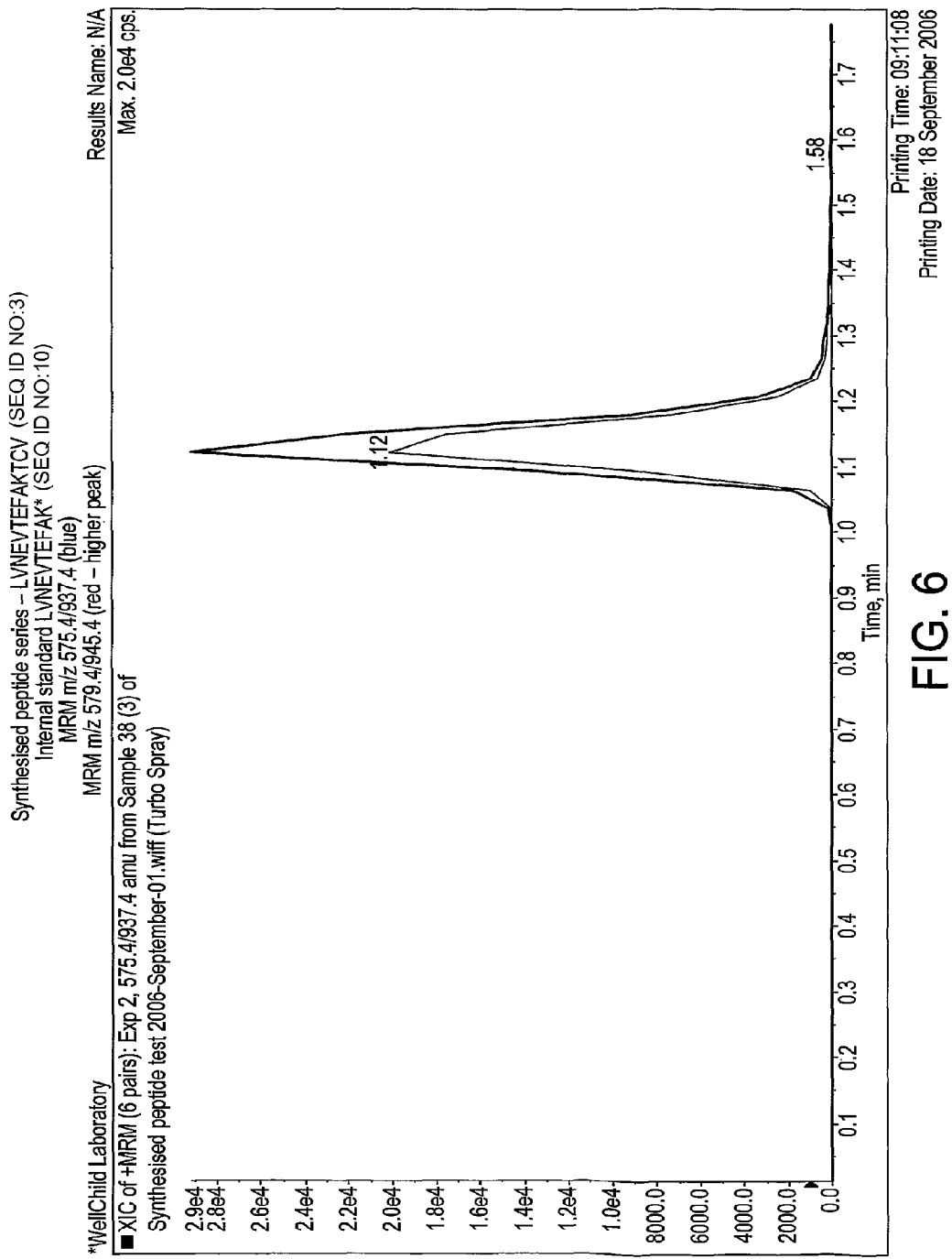
Figure 7:
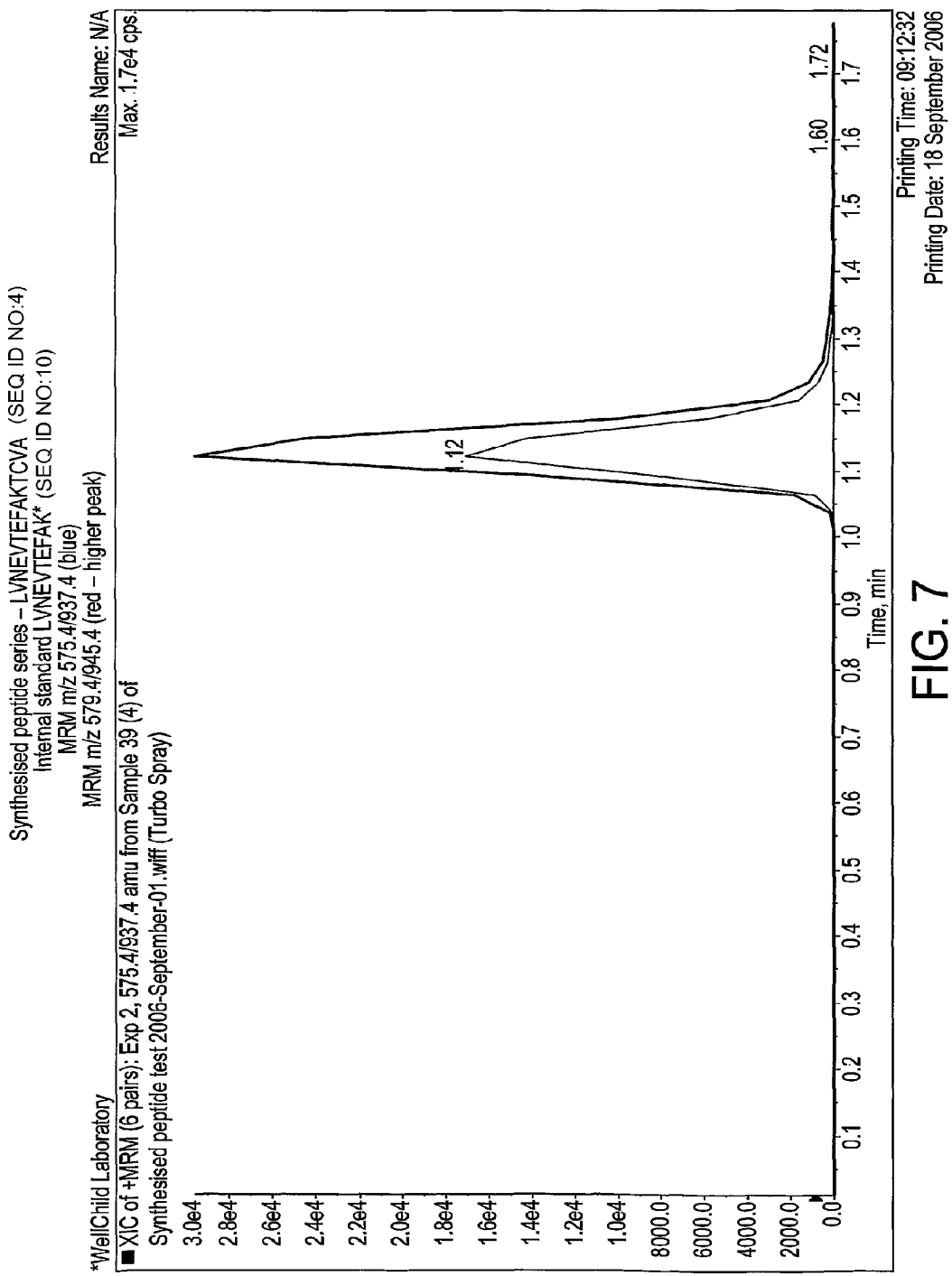
Figure 8:
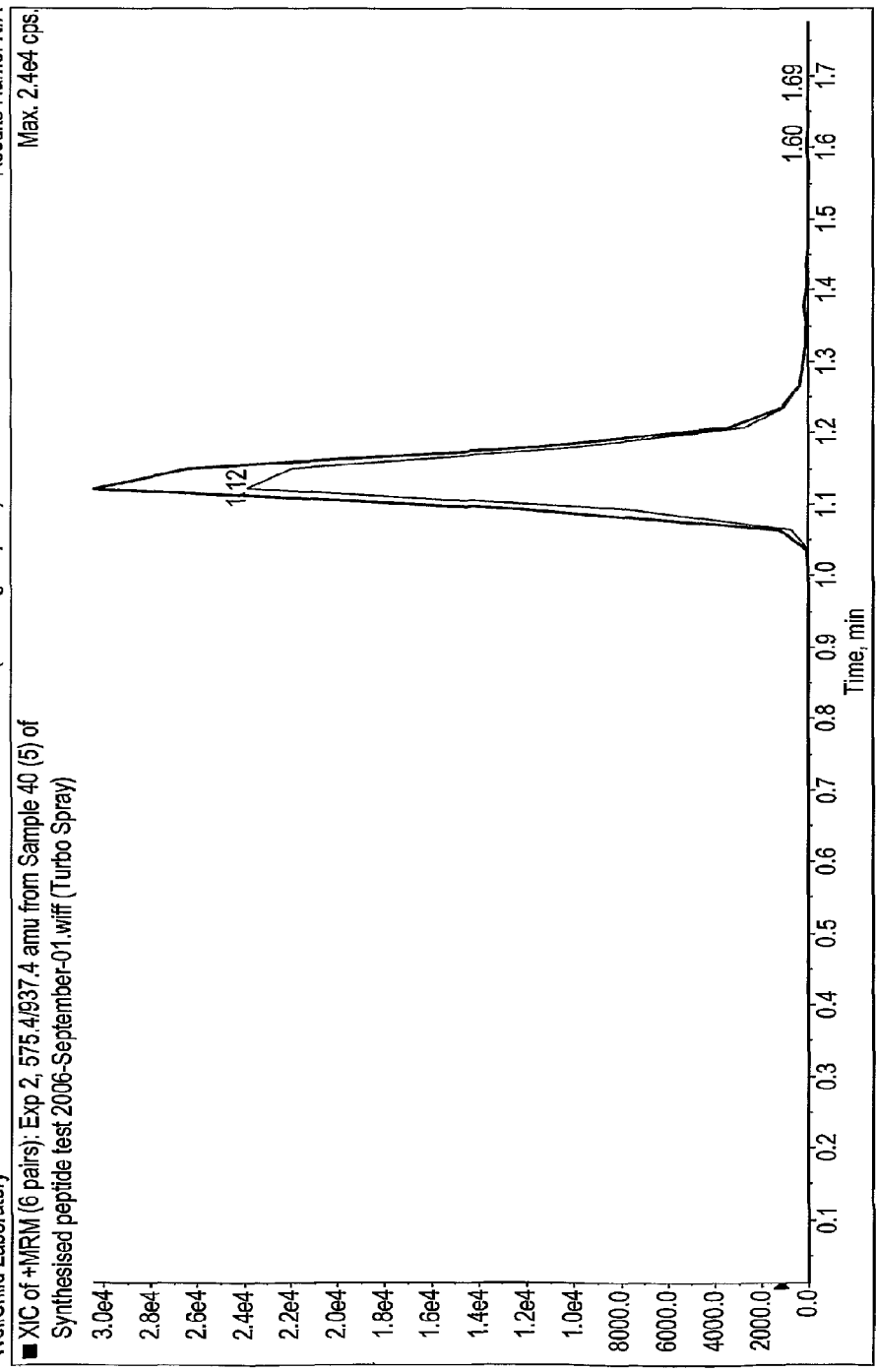
Figure 9:
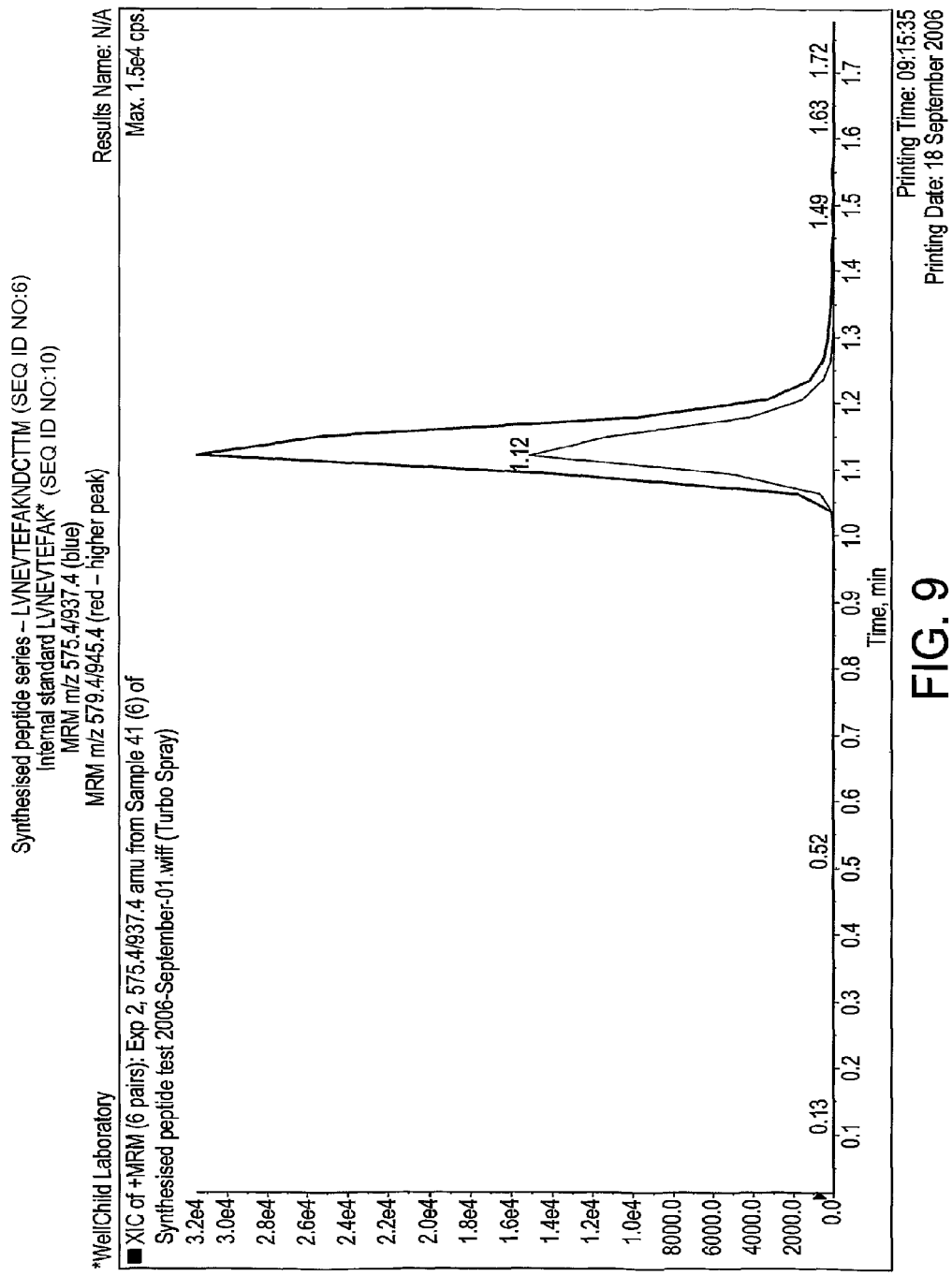
Figure 10:
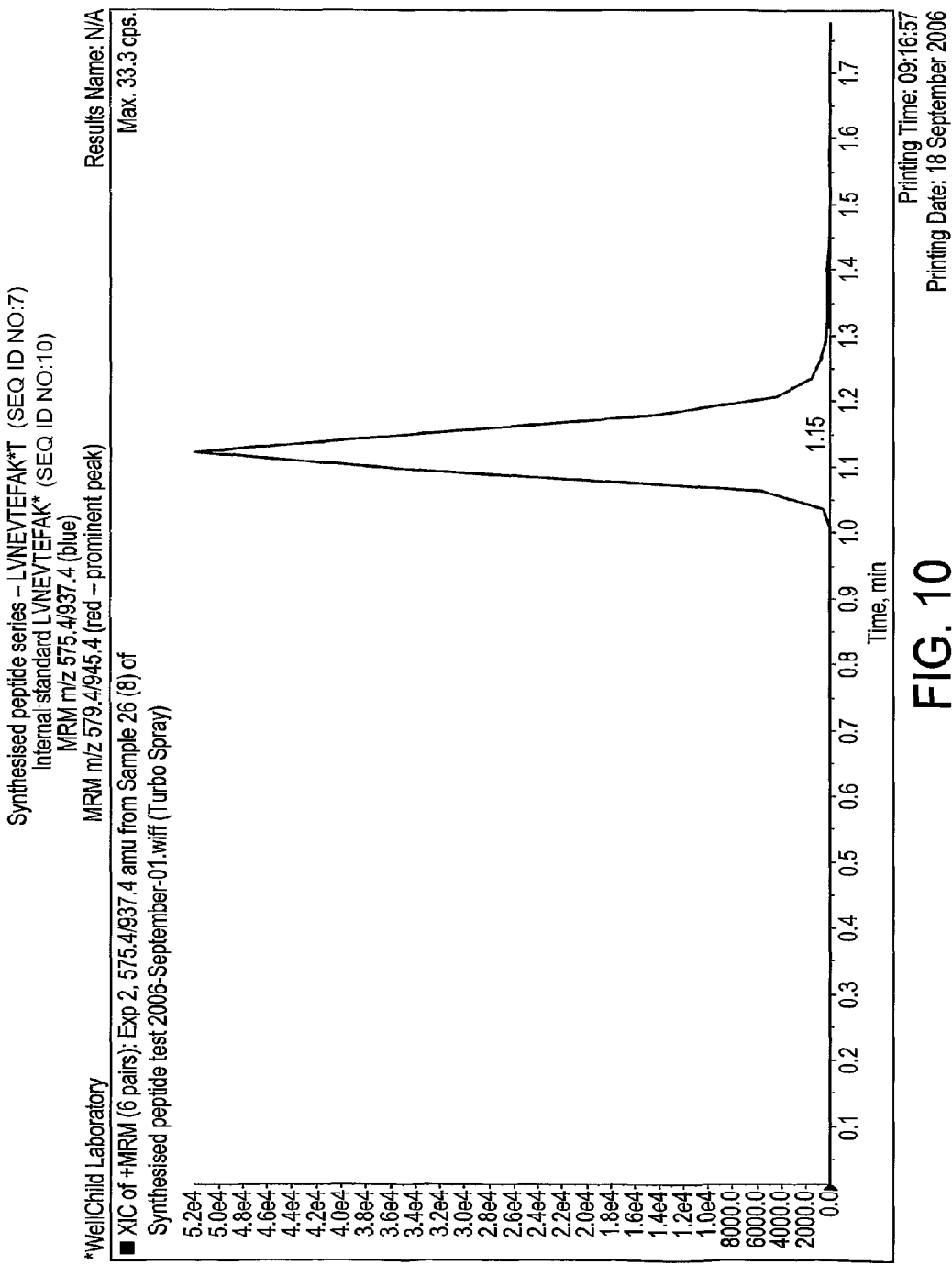

We have synthesised a stable isotope labelled peptide (the C-terminal lysine U-13C6, U-15N2 labelled) that allows us to quantitatively measure the T6 peptide of human albumin (LVNEVTEFAK*) (SEQ ID NO:10). This is for comparison (not part of the invention) and gives us no information on digestion.

However if we use a peptide standard according to the present invention such as LVNEVTEFAK*T (SEQ ID NO:7) (T is the first amino acid of T7) this requires digestion to release LVNEVTEFAK* (SEQ ID NO:10), providing information on digestion and correcting for ion suppression.

We test peptides including up to 5 of the first amino acids of T7 to see how necessary they may be. Analysis of the active site of trypsin suggests that we need only the one amino acid. Even if we add a C-terminal extension of up to 6 amino acids the synthesis is relatively simple and cheap (unlike production by protein expression). This can be applied to any protein analysis.

Method

We have demonstrated this using the T6 peptide of albumin as a model. The amino acid sequence of the T6 peptide of human albumin is LVNEVTEFAK (SEQ ID NO:10). We have produced the T6 peptide plus between 1 and 5 of the T7 amino acids, i.e.

```
                                    (SEQ ID NO: 7)
         LVNEVTEFAKT               (peptide 1)

(SEQ ID NO: 9)
         LVNEVTEFAKTC              (peptide 2)

(SEQ ID NO: 3)
         LVNEVTEFAKTCV             (peptide 3)

(SEQ ID NO: 4)
         LVNEVTEFAKTCVA            (peptide 4)

(SEQ ID NO: 5)
         LVNEVTEFAKTCVAD           (peptide 5)
```

In addition, we have had the T6 peptide and the: T6+1 peptide synthesised with lysine labelled with 6 carbon 13 and 2 nitrogen 15 atoms, i.e. LVNEVTEFAK* (SEQ ID NO:10) (peptide 7) and LVNEVTEFAK*T (SEQ ID NO:7) (peptide 8).

The first experiment was test the hypothesis that the LVNEVTEFAKT (SEQ ID NO:7) peptide is cleaved to LVNEVTEFAK (SEQ ID NO:10) by trypsin as efficiently as the longer peptides. Using LVNEVTEFAK* (SEQ ID NO:10) as the internal standard peptides (1-5, and 8) were digested using standard protocol. The results were conclusive: peptides 1, 3, 4, and 5 demonstrated an equivalent signal for LVNEVTEFAK (SEQ ID NO:10) using 3 different MRMs. Tryptic digestion of peptide 8 demonstrated no signal for LVNEVTEFAK (SEQ ID NO:10) but the LVNEVTEFAK* (SEQ ID NO:10) signal increased by the expected amount. The surprise was with peptide 2, LVNEVTEFAKTC (SEQ ID NO:9), where there was virtually no signal for LVNEVTEFAK (SEQ ID NO:10) (disulphide formation?). This implies that any internal standard peptide where cysteine is the N-terminal amino acid will require the next amino acid in addition to be effective.

The second experiment was to demonstrate the function of the internal standard in an actual assay. Human albumin standard material was diluted over the range 25-1000 mg/l and digested using our standard protocol. LVNEVTEFAK*T (SEQ ID NO:7) was added to each sample as internal standard and the isotope ratio, LVNEVTEFAK (SEQ ID NO:10)/LVNEVTEFAK* (SEQ ID NO:10), was plotted against albumin concentration. Excellent linearity was observed for the T6 peptide using all 3 transitions. The T31, T34, and T70 peptides were included using the LVNEVTEFAK* (SEQ ID NO:10) signal and, as expected, the results were less good. The same experiment was repeated with human plasma initially diluted 1:40 (to approximately 1 g/l) and then diluted as the standard above. The lines are virtually superimposable.

Example 2

MS with Peptide Standards of the Invention

In this example we demonstrate stable isotope dilution quantitation of proteins using stable isotope labelling of peptides.

A problem is that stable isotope labelled peptides equivalent to the natural peptides released by tryptic digestion of a protein (example T6 peptide of albumin) will correct for ion suppression and efficiency of fragmentation but not efficacy of tryptic digestion.

According to the invention, addition of natural sequence amino acids to the C-terminal arginine/lysine labelled stable isotope will correct for efficacy of tryptic digestion, ion suppression, and efficiency of peptide fragmentation Note only C-terminal lysine/arginine are labelled, the charge will tend to be localised with the lysine/arginine and the y series product ion fragments for quantitation will retain the stable isotope label.

This example investigates whether addition of just one amino acid to the stable isotope labelled arginine/lysine at the C-terminal end of a peptide normally released by trypsin is sufficient to correct for efficacy of tryptic digestion, ion suppression, and efficiency of peptide fragmentation.

It should be noted that increasing the number of sequence amino acids and/or non sequence amino acids will also work, but according to the invention the peptide standard length is advantageously minimised which provides advantages such as lower cost, lower complexity, easier recovery and others.

Experiment to Determine Number of Amino Acids Required Following Trypsin Digest Site for Digestion.

|   | Peptides | Mol wt | Concentration (g/l) | Concentration (mmol/l) | Assay concentration (μmol/l) |
|---|---|---|---|---|---|
| 1 | LVNEVTEFAKT (SEQ ID NO: 7) | 1249.7 | 1 | 0.800 | 16.0 |
| 2 | LVNEVTEFAKTC (SEQ ID NO: 9) | 1352.6 | 1 | 0.739 | 14.8 |
| 3 | LVNEVTEFAKTCV (SEQ ID NO: 3) | 1451.7 | 1 | 0.689 | 13.8 |
| 4 | LVNEVTEFAKTCVA (SEQ ID NO: 4) | 1522.8 | 1 | 0.657 | 13.1 |
| 5 | LVNEVTEFAKTCVAD (SEQ ID NO: 5) | 1637.8 | 1 | 0.611 | 12.2 |
| 6 | LVNEVTEFAKNDCTTM (SEQ ID NO: 6) | 1813.8 | 0.5 | 0.276 | 11.0 |
| 8 | LVNEVTEFAK*T (SEQ ID NO: 7) | 1257.7 | 0.5 | 0.398 | 15.9 |
| Internal-std | LVNEVTEFAK* (SEQ ID NO: 10) | 1156.6 | 1 | 0.865 | 17.3 |

K* is lysine labelled with with 6 carbon 13 and 2 nitrogen 15 atoms.
Peptides 1, 2, 3, 4, 5, and internal std were diluted to c.1 mg/l (based on suppliers stated weight, NB not 100% peptide) with deionised water
Peptides 6 and 8 appeared difficult to dissolve, final concentration c. 500 μg/l
Peptides stored at −80° C. in 2 ml aliquots
Peptides, 1 mg/l, diluted 1:50 with deionised water and 500 μg/l 1:25 for experiment Assay
50 μl peptide 1-6 & 8 (blank was deionised water)+50 μl internal std
Add 10 μl acetonitrile & 10 μl 1% formic acid, vortex mix, and stand for 5 min
Add 6 μl 1 μM ammonium bicarbonate & 5 μl trypsin (5 mg/l), vortex mix, and pulse centrifuge (6 sec)
Incubate at 37° C. for 30 min & add 500 μl HPLC solvent (acetonitrile:water 1:1 with 0.025% formic acid)
Vortex mix and transfer to 96-deep well polypropylene plate
Sample volume, 5 μl; flow rate, 500 μl/min
Chromatography—teicoplanin guard column
MSMS parameters—generic peptide ionisation and doubly charged ion fragmentation T6 doubly charged ion m/z 575.4 and internal std m/z 579.4
Product ions (m/z): 937.4, 823.4, 694.4—internal std (m/z): 945.4, 831.4, 702.4 (150 ms/MRM)
Results

| Sample Name/ID | Analyte | Analyte Peak Area (counts) | Area Ratio | IS Peak Area (counts) | Analyte Peak Area/μmol/l peptide (AP) | AP/IS peak area |
|---|---|---|---|---|---|---|
| Blank | T6 694 | 212 | 0.00165 | 128000 | | |
| 1 | T6 694 | 124000 | 1.01000 | 122000 | 7748 | 0.064 |
| 2 | T6 694 | 1350 | 0.01040 | 130000 | 91 | 0.001 |
| 3 | T6 694 | 84500 | 0.66900 | 126000 | 6133 | 0.049 |
| 4 | T6 694 | 68000 | 0.53300 | 127000 | 5178 | 0.041 |
| 5 | T6 694 | 92500 | 0.72800 | 127000 | 7575 | 0.060 |
| 6 | T6 694 | 51000 | 0.39500 | 129000 | 4625 | 0.036 |
| 8 | T6 694 | 149 | 0.00062 | 238000 | | |
| Blank | T6 823 | 93 | 0.00204 | 45800 | | |
| 1 | T6 823 | 49400 | 1.13000 | 43900 | 3087 | 0.070 |
| 2 | T6 823 | 469 | 0.01020 | 46000 | 32 | 0.001 |
| 3 | T6 823 | 32100 | 0.68700 | 46800 | 2330 | 0.050 |
| 4 | T6 823 | 26900 | 0.58300 | 46100 | 2048 | 0.044 |
| 5 | T6 823 | 37700 | 0.80000 | 47200 | 3087 | 0.065 |
| 6 | T6 823 | 19900 | 0.42200 | 47200 | 1805 | 0.038 |
| 8 | T6 823 | 62 | 0.00074 | 83000 | | |
| Blank | T6 937 | 101 | 0.00078 | 130000 | | |
| 1 | T6 937 | 144000 | 1.13000 | 128000 | 8998 | 0.070 |
| 2 | T6 937 | 1760 | 0.01380 | 128000 | 119 | 0.001 |
| 3 | T6 937 | 94600 | 0.71200 | 133000 | 6867 | 0.052 |
| 4 | T6 937 | 81600 | 0.58800 | 139000 | 6213 | 0.045 |
| 5 | T6 937 | 109000 | 0.80200 | 136000 | 8926 | 0.066 |
| 6 | T6 937 | 56800 | 0.42600 | 133000 | 5151 | 0.039 |
| 8 | T6 937 | 147 | 0.00058 | 253000 | | |

In addition, results are presented in FIGS. 2 to 10.

| | Internal standard area | | |
|---|---|---|---|
| | T6 694 | T6 823 | T6 937 |
| Mean (Blank, 1-6) | 127000 | 46143 | 132429 |
| IS + peptide 8 | 238000 | 83000 | 253000 |
| Ratio | 1.87 | 1.80 | 1.91 |

Thus it is demonstrated that only one C-terminal amino acid addition (i.e. a C-terminal extension of only 1 amino acid) is required for digestion.
It is shown that with addition of one amino acid the release of target peptide is at least as good as with 3, 4, 5 and 6 amino acids within the limits of the experiment (initial peptide concentration not physically measured).

Addition of more than one amino acid in the sequence (i.e. C-terminal extension of 2 to 5 or 6 amino acids or even more) or use of a non-sequence set of amino, acids (i.e. sequence of C-terminal extension not based on corresponding amino acids from parent polypeptide) is also usable if desired by the operator.

It should be noted that with cysteine as the C-terminal peptide there is limited digestion. Thus, preferably Cysteine is not the C-terminal peptide. Without wishing to be bound by theory, this effect may be due to formation of disulphide bonds/binding interference.

Addition of peptide 8, the preferred internal standard to correct for efficiency of tryptic digestion, ion suppression, and peptide fragmentation, indicates full recovery, within the limits of the experiment.

The signals for the 3 MRMs are, as expected, different but are consistent between the peptides.

The internal standard used in this experiment (no C-terminal extension—not part of the invention—for comparison purposes only) cannot correct for efficiency of tryptic digestion but does correct for ion suppression and peptide fragmentation (column I).

Thus it is shown that in accordance with the present invention a peptide standard such as LVNEVTEFAK*T (SEQ ID NO:7) is the simplest consistent peptide sequence that will correct for efficiency of tryptic digestion, ion suppression, and fragmentation. In this example, these criteria were assessed in the context of the T6 peptide of albumin.

Stable isotope labelling of tryptic peptides at the C-terminal arginine/lysine and addition of at least one further amino acid (normally the next sequential amino acid) as the C-terminal extension is demonstrated as a general principle.

Other proteolytic enzymes (preferably endopeptidases) can be employed in the same manner, adjusting for their recognition sequence/cleavage site as required.

Example 3

Application to Analysis of Non-Matching Peptides

The peptide standards of the invention need not correspond precisely to the target peptide being detected. For example, peptide standards based on the T6 albumin peptide have, been demonstrated in the above examples in analysis of the T6 albumin peptide itself. However, T6-based peptide standards find application in analysis of any other peptide since they provide the same internal control information regardless of what target peptide is focussed on when interpreting the results. In particular, in this example the T6 based peptide standards of the invention are used in analysis of other peptides, for example the T31, T34, T70 peptides or any other peptide of interest. This applies equally to use as conventional peptide standards or as internal peptide standards.

Example 4

Quantitative Measurement of Plasma Albumin Using Peptide Based Analysis

Quantitation of T6 peptide (LVNEYTEFAK) (SEQ ID NO:10) by stable isotope dilution liquid chromatography electrospray mass spectrometry-mass spectrometry Stable isotope internal standard, LVNEYTEFAK*T (SEQ ID NO:7) (see above for labelling)

Precision and Comparative Data

Expt 1. Intra-assay precision of MSMS, plasma assayed 6 times

Expt 2. Blank, albumin std (82.2 mg/l), Dade Behring plasma albumin controls (L, M, H), and 36 anonymised plasma samples were measured on a Dade Behring BN Prospec laser nephelometry (according to manufacturer's instructions) and by MSMS Plasma diluted 1:100 with deionised water
Internal standard, LVNEVTEFAK*T (SEQ ID NO:7) (c. 500 µg/l) diluted 1:50 with deionized water
Assay
50 µl blank/standard+50 µl internal std
Add 10 µl acetonitrile & 10 µl 1% formic acid, vortex mix, and stand for 5 min
Add 6 µl 1M ammonium bicarbonate & 10 µl trypsin (5 mg/l), vortex mix, and pulse centrifuge (6 sec)
Incubate at 37° C. for 30 min & add 250 µl running solvent (acetonitrile:water (1:1) with 0.025% formic acid)
Vortex mix and transfer to 96-deep well polypropylene plate
Sample volume, 5 µl; flow rate, 500 µl/min
Chromatography—Chirobiotic T 100×2.1 mm column with a 2 cm×4.0 mm guard column (Advanced Separation Technologies, Congleton, U.K.)
MSMS parameters—generic peptide ionisation and doubly charged ion fragmentation
T6 doubly charged ion m/z 575.4 and internal std m/z 579.4
Product ions (m/z): 937.4, 823.4, 694.4—internal std (m/z): 945.4, 831.4, 702.4 (150 ms/MRM)
Note: additional MRM acquisitions (150 ms each) for the T31 peptide (m/z 337.3/416.3), T34 peptide (m/z 441.0/680.5), T70 peptide (m/z 501.2/587.5), and T6 peptide (m/z 575.4/937.4) were included
Results
NB Results are calculated by dividing the analyte area by the equivalent internal standard area, the isotope ratio (IR). Only data for the T6 peptide (m/z 575.4/937.4, 579.4/945.4) are presented. Comparable data were obtained for the less sensitive transitions on the T6 peptide
Precision Experiment:
Mean albumin concentration 43.3 g/l, CV 4.51% (see ALB precision and comparison data presented below and see FIGS. 11 and 12)
Comparison Experiment
The Dade Behring control values were, plasma albumin (g/l):

| Control | BN Prospec Result | MSMS result | Mean MSMS result | Expected range (manufacturer's) |
|---|---|---|---|---|
| L | 29.8 | 30.0, 31.8 | 30.9 | 26.3-35.5 |
| M | 42.7 | 52.4, 45.1 | 48.8 | 39.6-53.6 |
| H | 58.7 | 68.2, 75.8 | 72.0 | 55.6-75.3 |

(see ALB precision and comparison data presented below and see FIGS. 11 and 12)

Figure 11:
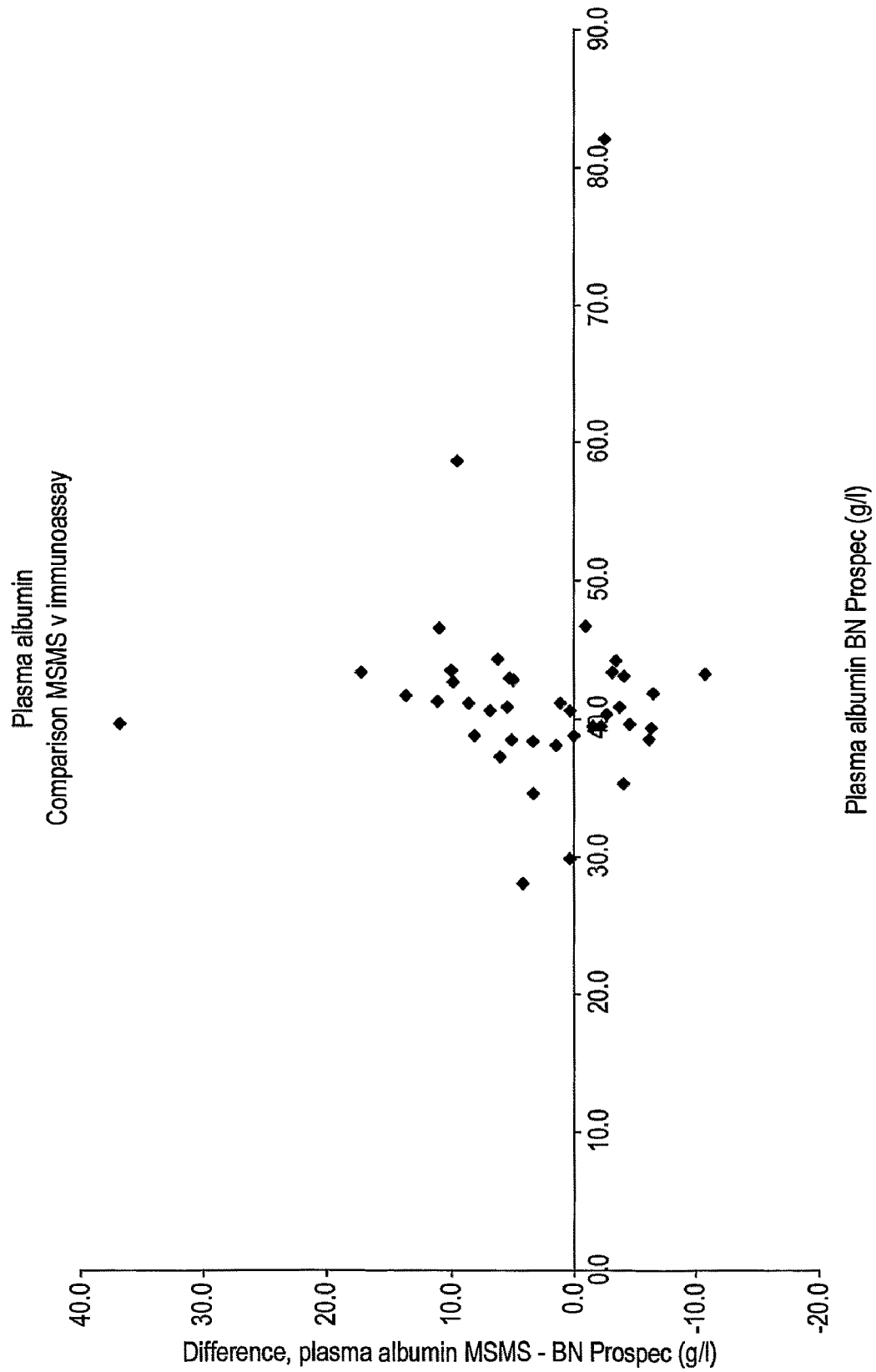
FIG. 11 shows a scatterchart.

On average the calculated plasma albumin concentration calculated by stable isotope dilution of the T6 peptide was 3 g/l (range 36.9 to −10.8 g/l) higher than that measured by the Dade Behring laser nephelometer immunoassay (see difference plot FIG. 11)

Figure 12:
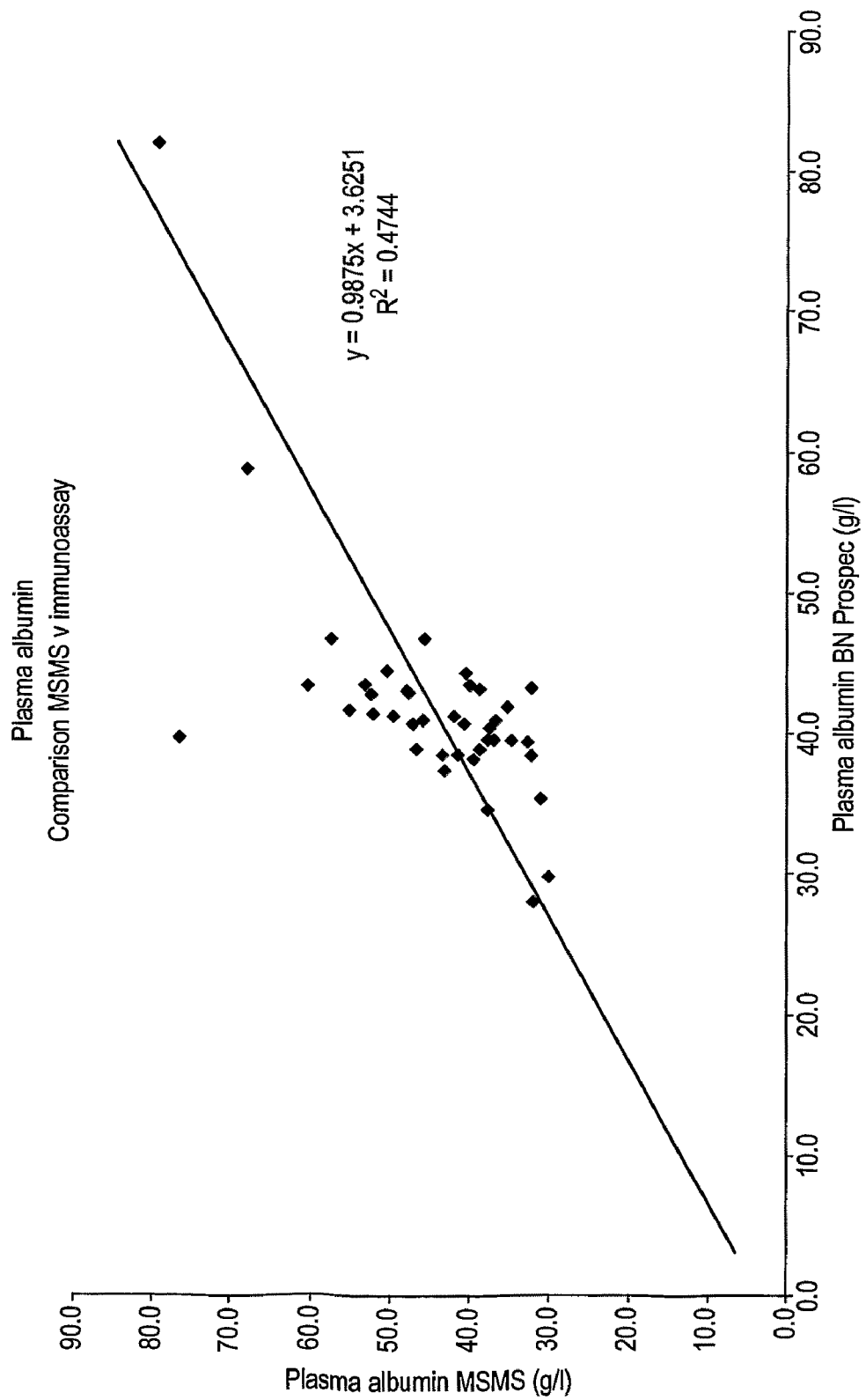
FIG. 12 shows a graph.

The correlation was highly significant, r=0.6888 (see correlation plot FIG. 12)

Measuring plasma albumin using stable isotope (LVNEVTEFAK*T) (SEQ ID NO:7) dilution of the T6 peptide proved precise at 4.5%. This is in agreement with data presented in the earlier examples. Equivalent data on dye binding or immuno based assays are not presented, but 5% is considered reasonable. Note the wide control value ranges (see above) quoted for the Dade Behring immunoassay.

Given the specificity of the stable isotope dilution MSMS method and the diagnostic industry use of stable isotope dilution MSMS methods as reference methods, the performance of the immunoassay might be considered disappointing. There is no easily applied "gold" standard method. The Dade Behring immunoassay was taken as the reference method for comparison. Without wishing to be bound by theory, it should be noted that the two methods are measuring different things.

We present the first direct comparison of a peptide based stable isotope dilution MSMS measurement of a clinically diagnostic protein with an established clinical immunoassay. The results indicate that MSMS measurement using the concept of the invention (i.e. peptide stable isotope plus 1-6 amino acids, in this example one amino acid, as internal standard) is both precise and clinically useful. As a means of measuring clinically diagnostic proteins the MSMS system offers a significant multiplexing capability that may prove more valuable than the perceived ease of use of dye binding and immunoassay systems. Thus the utility and performance of the invention is demonstrated.

Correlation (FIG. 12) and difference (FIG. 11) plots determined using highlighted (asterisked) data:

| Correlation Sample Name | Sample Type | Analyte Peak Name | albumin T6 Calculated Concentration (g/l) | BN Prospec Albumin (g/l) | Difference |
|---|---|---|---|---|---|
| Blank | Standard | albumin T6 | | | |
| Alb std 82 g/l | Standard | albumin T6 | 79.4 | 82.0* | −2.6 |
| DB LQC | Unknown | albumin T6 | 30.0 | 29.8* | 0.2 |
| DB MQC | Unknown | albumin T6 | 52.4 | 42.7* | 9.7 |
| DB HQC | Unknown | albumin T6 | 68.2 | 58.7* | 9.5 |
| P1 | Unknown | albumin T6 | 40.1 | 43.3* | −3.2 |
| P2 | Unknown | albumin T6 | 38.7 | 38.8* | −0.1 |
| P3 | Unknown | albumin T6 | 32.9 | 39.3* | −6.4 |
| P4 | Unknown | albumin T6 | 32.2 | 38.4* | −6.2 |
| P5 | Unknown | albumin T6 | 43.2 | 37.2* | 6.0 |
| P6 | Unknown | albumin T6 | 49.6 | 41.1* | 8.5 |
| P7 | Unknown | albumin T6 | 31.2 | 35.3* | −4.1 |
| P8 | Unknown | albumin T6 | 57.5 | 46.6* | 10.9 |
| P9 | Unknown | albumin T6 | 47.7 | 42.8* | 4.9 |
| P10 | Unknown | albumin T6 | 32.0 | 28.0* | 4.0 |
| P11 | Unknown | albumin T6 | 37.6 | 40.3* | −2.7 |
| P12 | Unknown | albumin T6 | 52.3 | 41.3* | 11.0 |
| P13 | Unknown | albumin T6 | 37.8 | 39.4* | −1.6 |
| P14 | Unknown | albumin T6 | 32.4 | 43.2* | −10.8 |
| P15 | Unknown | albumin T6 | 45.7 | 46.7* | −1.0 |
| P16 | Unknown | albumin T6 | 60.5 | 43.3* | 17.2 |
| P17 | Unknown | albumin T6 | 43.4 | 38.4* | 5.0 |
| P18 | Unknown | albumin T6 | 36.9 | 40.8* | −3.9 |
| P19 | Unknown | albumin T6 | 53.3 | 43.4* | 9.9 |
| P20 | Unknown | albumin T6 | 41.6 | 38.3* | 3.3 |
| P21 | Unknown | albumin T6 | 46.1 | 40.8* | 5.3 |
| P22 | Unknown | albumin T6 | 40.6 | 44.1* | −3.5 |
| P23 | Unknown | albumin T6 | 37.8 | 34.5* | 3.3 |
| P24 | Unknown | albumin T6 | 46.7 | 38.7* | 8.0 |
| P25 | Unknown | albumin T6 | 39.5 | 38.1* | 1.4 |
| P26 | Unknown | albumin T6 | 35.3 | 41.8* | −6.5 |
| P27 | Unknown | albumin T6 | 37.1 | 39.4* | −2.3 |
| P28 | Unknown | albumin T6 | 76.5 | 39.6* | 36.9 |
| P29 | Unknown | albumin T6 | 47.3 | 40.6* | 6.7 |
| P30 | Unknown | albumin T6 | 40.8 | 40.5* | 0.3 |
| P31 | Unknown | albumin T6 | 38.8 | 43.0* | −4.2 |
| P32 | Unknown | albumin T6 | 34.9 | 39.5* | −4.6 |
| P33 | Unknown | albumin T6 | 42.1 | 41.1* | 1.0 |
| P34 | Unknown | albumin T6 | 55.2 | 41.6* | 13.6 |
| P35 | Unknown | albumin T6 | 48.0 | 42.9* | 5.1 |
| P36 | Unknown | albumin T6 | 50.4 | 44.3* | 6.1 |
| Blank | Standard | albumin T6 | | | |
| Alb std 82 g/l | Standard | albumin T6 | 84.6 | 82.0 Mean | 3.1 |
| DB LQC | Unknown | albumin T6 | 31.8 | 29.8 | |
| DB MQC | Unknown | albumin T6 | 45.1 | 42.7 | |
| DB HQC | Unknown | albumin T6 | 75.8 | 58.7 | |

Intra-Assay Precision
Plasma Sample Diluted 1:100—Six Separate Dilutions

| | Calculated concentration (g/l) |
|---|---|
| | 46.0 |
| | 41.2 |
| | 44.4 |
| | 41.8 |
| | 41.8 |
| | 44.6 |
| Mean | 43.3 |
| SD | 1.95 |
| CV % | 4.51 |

All publications mentioned in the above specification are herein incorporated by reference. Various modifications and variations of the described aspects and embodiments of the present invention will be apparent to those skilled in the art without departing from the scope of the present invention. Although the present invention has been described in connection with specific preferred embodiments, it should be understood that the invention as claimed should not be unduly limited to such specific embodiments. Indeed, various modifications of the described modes for carrying out the invention which are obvious to those skilled in this or related fields are intended to be within the scope of the following claims.

The invention claimed is:

1. A method for making a peptide standard for mass spectrometry said method comprising
   (a) identifying endopeptidase cleavage sites in a parent polypeptide sequence of interest;
   (b) selecting peptide sequences from said parent polypeptide which are defined by the endopeptidase cleavage sites of step (a),
   (c) adding a C-terminal extension to each selected sequence,
   wherein if the endopeptidase cleavage site is C-terminal to its recognition sequence then the C-terminal extension comprises 1 to 6 amino acids,
   wherein if the endopeptidase cleavage site is N-terminal to its recognition sequence then the C-terminal extension comprises said recognition sequence,
   wherein if the endopeptidase cleavage site is within its recognition sequence then the C-terminal extension comprises the remainder of said recognition sequence C-terminal to the cleavage site; and
   (d) synthesising a peptide having the extended amino acid sequence of step (c).

2. A method according to claim 1 wherein the 1 to 6 amino acids of step (c) are identical to the 1 to 6 amino acids which immediately follow the endopeptidase recognition site in the polypeptide sequence of interest.

3. A method according to claim 1 wherein the 1 to 6 amino acids of step (c) are 1 to 5 amino acids and said 1 to 5 amino acids are TCVAD (SEQ ID NO:2).

4. A method according to claim 1 wherein synthesis of the peptide is by chemical means.

5. A method according to claim 1 wherein said peptide is labelled with stable isotope.

6. A method according to claim 5 wherein said isotope is carbon 13 and/or nitrogen 15.

7. A method according to claim 1 wherein said endopeptidase is a single endopeptidase.

8. A method according to claim 1 wherein said endopeptidase is selected from the group consisting of trypsin and V8.

9. A method according to claim 8 wherein said endopeptidase is trypsin.

10. A method according to claim 1 wherein the parent polypeptide is albumin.

11. A method for analysing a sample by mass spectrometry said method comprising
 (a) providing a peptide standard prepared by the method according to claim 1 and a sample;
 (b) digesting said sample and peptide standard with the appropriate endopeptidase;
 (c) subjecting the treated sample and peptide standard to mass spectrometry analysis.

12. A method according to claim 11 wherein digesting said sample and peptide standard with the appropriate endopeptidase comprises the steps of
 (i) adding said peptide standard to said sample
 (ii) contacting the mixture of step (i) with the appropriate endopeptidase.

13. An isolated polypeptide consisting of an amino acid sequence selected from the group consisting of LVNEVTEFAKT (SEQ ID NO:7), LVNEVTEFAKTC (SEQ ID NO:9), LVNEVTEFAKTCV (SEQ ID NO:3), LVNEVTEFAKTCVA (SEQ ID NO:4), and LVNEVTEFAKTCVAD (SEQ ID NO:5), wherein the polypeptide is optionally labeled with one or more stable isotope.

* * * * *

```
                       SEQUENCE LISTING

<160> NUMBER OF SEQ ID NOS: 10

<210> SEQ ID NO 1
<211> LENGTH: 6
<212> TYPE: PRT
<213> ORGANISM: Artificial Sequence
<220> FEATURE:
<223> OTHER INFORMATION: Synthetic - Extension

<400> SEQUENCE: 1

Asn Asp Cys Thr Thr Met
1               5

<210> SEQ ID NO 2
<211> LENGTH: 5
<212> TYPE: PRT
<213> ORGANISM: Artificial Sequence
<220> FEATURE:
<223> OTHER INFORMATION: Synthetic - Extension

<400> SEQUENCE: 2

Thr Cys Val Ala Asp
1               5

<210> SEQ ID NO 3
<211> LENGTH: 13
<212> TYPE: PRT
<213> ORGANISM: Artificial Sequence
<220> FEATURE:
<223> OTHER INFORMATION: Synthetic - Peptide

<400> SEQUENCE: 3

Leu Val Asn Glu Val Thr Glu Phe Ala Lys Thr Cys Val
1               5                   10

<210> SEQ ID NO 4
<211> LENGTH: 14
<212> TYPE: PRT
<213> ORGANISM: Artificial Sequence
<220> FEATURE:
<223> OTHER INFORMATION: Synthetic - Peptide

<400> SEQUENCE: 4

Leu Val Asn Glu Val Thr Glu Phe Ala Lys Thr Cys Val Ala
1               5                   10

<210> SEQ ID NO 5
<211> LENGTH: 15
<212> TYPE: PRT
<213> ORGANISM: Artificial Sequence
<220> FEATURE:
<223> OTHER INFORMATION: Synthetic - Peptide

<400> SEQUENCE: 5

Leu Val Asn Glu Val Thr Glu Phe Ala Lys Thr Cys Val Ala Asp
1               5                   10                  15

<210> SEQ ID NO 6
<211> LENGTH: 16
```

```
<212> TYPE: PRT
<213> ORGANISM: Artificial Sequence
<220> FEATURE:
<223> OTHER INFORMATION: Synthetic - Peptide

<400> SEQUENCE: 6

Leu Val Asn Glu Val Thr Glu Phe Ala Lys Asn Asp Cys Thr Thr Met
1               5                   10                  15

<210> SEQ ID NO 7
<211> LENGTH: 11
<212> TYPE: PRT
<213> ORGANISM: Artificial Sequence
<220> FEATURE:
<223> OTHER INFORMATION: Synthetic - Peptide

<400> SEQUENCE: 7

Leu Val Asn Glu Val Thr Glu Phe Ala Lys Thr
1               5                   10

<210> SEQ ID NO 8
<211> LENGTH: 4
<212> TYPE: PRT
<213> ORGANISM: Artificial Sequence
<220> FEATURE:
<223> OTHER INFORMATION: Synthetic - Peptide

<400> SEQUENCE: 8

Asn Asp Cys Thr
1

<210> SEQ ID NO 9
<211> LENGTH: 12
<212> TYPE: PRT
<213> ORGANISM: Artificial Sequence
<220> FEATURE:
<223> OTHER INFORMATION: Synthetic - Peptide

<400> SEQUENCE: 9

Leu Val Asn Glu Val Thr Glu Phe Ala Lys Thr Cys
1               5                   10

<210> SEQ ID NO 10
<211> LENGTH: 10
<212> TYPE: PRT
<213> ORGANISM: Artificial Sequence
<220> FEATURE:
<223> OTHER INFORMATION: Synthetic - Internal Standard

<400> SEQUENCE: 10

Leu Val Asn Glu Val Thr Glu Phe Ala Lys
1               5                   10
```